United States Patent
Nagase et al.

(10) Patent No.: US 8,632,457 B2
(45) Date of Patent: Jan. 21, 2014

(54) RECEIVING APPARATUS AND IN-VIVO INFORMATION ACQUIRING SYSTEM USING THE SAME

(75) Inventors: Ayako Nagase, Hachioji (JP); Seiichiro Kimoto, Hachioji (JP); Manabu Fujita, Hino (JP); Toshiaki Shigemori, Hachioji (JP); Akira Matsui, Hino (JP); Kazutaka Nakatsuchi, Hino (JP)

(73) Assignee: Olympus Corporation (JP)

( * ) Notice: Subject to any disclaimer, the term of this patent is extended or adjusted under 35 U.S.C. 154(b) by 1185 days.

(21) Appl. No.: 12/090,688

(22) PCT Filed: Oct. 19, 2006

(86) PCT No.: PCT/JP2006/320865
§ 371 (c)(1),
(2), (4) Date: Aug. 24, 2009

(87) PCT Pub. No.: WO2007/046476
PCT Pub. Date: Apr. 26, 2007

(65) Prior Publication Data
US 2010/0016661 A1 Jan. 21, 2010

(30) Foreign Application Priority Data

Oct. 19, 2005 (JP) .................................. 2005-304963

(51) Int. Cl.
*A61B 1/00* (2006.01)
*A61B 1/04* (2006.01)
(52) U.S. Cl.
USPC ........... 600/103; 600/109; 600/117; 600/118; 455/132; 455/134
(58) Field of Classification Search
USPC ................. 600/109, 118, 160, 407, 424, 103; 455/132, 134
See application file for complete search history.

(56) References Cited

U.S. PATENT DOCUMENTS

| | | | |
|---|---|---|---|
| 7,022,067 B2 | 4/2006 | Glukhovsky et al. | 600/109 |
| 7,215,338 B2 * | 5/2007 | Horn et al. | 345/440 |
| 7,918,786 B2 * | 4/2011 | Kawano et al. | 600/117 |

(Continued)

FOREIGN PATENT DOCUMENTS

| | | |
|---|---|---|
| JP | 2003-19111 | 1/2003 |
| JP | 2003-70728 | 3/2003 |

(Continued)

OTHER PUBLICATIONS

Search Report issued by European Patent Office in connection with corresponding application No. EP 06 81 2043 on Oct. 22, 2010.

(Continued)

*Primary Examiner* — John P Leubecker
*Assistant Examiner* — Arnaldo Torres Diaz
(74) *Attorney, Agent, or Firm* — Ostrolenk Faber LLP

(57) ABSTRACT

An object of the invention is to receive, with a high sensitivity, a radio signal transmitted within a short time before a capsule endoscope reaches the stomach of a subject and acquire, in a satisfactory state, information on the interior of the subject such as image data picked up by the capsule endoscope. The receiving apparatus according to the invention includes a plurality of receiving antennas including a specified receiving antenna for receiving a radio signal from a capsule endoscope before the stomach is reached, a switching controller, an arrival determining unit and a mode switching unit. The switching controller performs a control operation for switching to and maintaining the receiving antenna in an initial mode or a control operation for switching to the receiving antennas in a normal mode. The arrival determining unit determines whether the capsule endoscope has reached the stomach or not. The mode switching unit instructs the switching controller to perform the control operation for switching to the initial mode, and upon determination that the stomach has been reached, gives the instruction to perform the control operation for switching to the normal mode.

6 Claims, 15 Drawing Sheets

(56) References Cited

U.S. PATENT DOCUMENTS

| | | |
|---|---|---|
| 2002/0198439 A1 | 12/2002 | Mizuno .................. 600/109 |
| 2003/0085994 A1 | 5/2003 | Fujita et al. |
| 2004/0111011 A1 | 6/2004 | Uchiyama et al. |
| 2005/0065407 A1 | 3/2005 | Nakamura et al. |
| 2005/0143643 A1 | 6/2005 | Mimai et al. |
| 2005/0183733 A1* | 8/2005 | Kawano et al. .............. 128/899 |

FOREIGN PATENT DOCUMENTS

| | | |
|---|---|---|
| JP | 2005-218502 | 8/2005 |
| JP | 2005-270462 | 10/2005 |
| JP | 2005-277739 | 10/2005 |
| JP | 2005-277740 | 10/2005 |
| WO | WO 2005/092189 | 10/2005 |

OTHER PUBLICATIONS

International Search Report mailed Jan. 23, 2007 in PCT International Application No. PCT/JP2006/320865.

Written Opinion mailed Jan. 23, 2007 in PCT International Application No. PCT/JP2006/320865.

* cited by examiner

RECEIVING APPARATUS AND IN-VIVO INFORMATION ACQUIRING SYSTEM USING THE SAME

CROSS-REFERENCE TO RELATED APPLICATIONS

The present application is a 35 U.S.C. §§371 national phase conversion of PCT/JP2006/320865, filed Oct. 19, 2006, which claims priority of Japanese Patent Application No. 2005-304963, filed Oct. 19, 2005, the disclosures of which have been incorporated herein by reference. The PCT International Application was published in the Japanese language.

TECHNICAL FIELD

The present invention relates to a receiving apparatus for receiving a radio signal from a mobile unit movable in a subject and acquiring various data (in-vivo information) in the subject based on the received radio signal, and an in-vivo information acquiring system using the apparatus.

BACKGROUND ART

In recent years, a capsule endoscope constituting a swallowable endoscope having an imaging function and a radio communication function has been proposed in the field of the endoscope, and an in-vivo information acquiring system for acquiring image data in the subject (an example of the in-vivo information) imaged by the capsule endoscope has been developed. In the in-vivo information acquiring system, the capsule endoscope is an example of the mobile unit movable in the subject for transmitting a radio signal including the data in the subject, and during the period before being naturally discharged from the subject after being swallowed by way of the mouth of the subject for observation (examination), moves in such organs as the stomach or the small intestine in accordance with the vermiculation thereof, while at the same time imaging the interior of the subject at predetermined intervals of, for example, 0.5 second.

While the capsule endoscope moves in the subject, the image data picked up by it is transmitted outside sequentially by radio communication, and received by the receiving apparatus through any one of a plurality of receiving antennas arranged dispersively outside the subject. The receiving apparatus demodulates the radio signal thus received through the receiving antenna into an image signal, and generates image data by executing a predetermined image processing on the image signal obtained. Thereafter, the receiving apparatus sequentially stores the image data thus generated (i.e. the image data picked up by the capsule endoscope) in a storage unit. A user such as a doctor or a nurse causes the image data stored in the receiving apparatus to be fetched into a work station, and the image of the interior of the subject is displayed on a display unit of the work station thereby to diagnose the subject (see Patent Document 1, for example).

When receiving the radio signal from the capsule endoscope introduced into the subject, the receiving apparatus switches to one of the plurality of receiving antennas dispersively arranged outside the subject which is suitable for receiving the radio signal, so as to receive the radio signal from the capsule endoscope through the particular receiving antenna. In this case, the receiving apparatus sequentially switches the receiving antenna for receiving the radio signal among the plurality of receiving antennas, while at the same time detecting a received electric field strength of the radio signal sequentially received through the plurality of receiving antennas. Thereafter, the receiving apparatus selects, among the plurality of receiving antennas, the receiving antenna from which the highest received electric field strength has been detected, and receives the radio signal from the capsule endoscope through the receiving antenna thus selected. By sequentially switching the receiving antenna suitable for receiving the radio signal among the plurality of receiving antennas in this way, the receiving apparatus can receive, with a satisfactory sensitivity, the radio signal from the capsule endoscope moving in the subject.

Patent Document 1: Japanese Patent Application Laid-Open No. 2003-19111

DISCLOSURE OF INVENTION

Problem to be Solved by the Invention

The capsule endoscope swallowed from the mouth of the subject, however, normally passes through the esophagus in a period of as short as about 4 seconds, and then reaches the stomach. In the conventional receiving apparatus described above, therefore, it is often difficult to select an optimum receiving antenna for receiving a radio signal among a plurality of receiving antennas and to receive the radio signal from the capsule endoscope through the optimum receiving antenna thus selected, within the short time before the capsule endoscope that has begun to pass through the esophagus reaches the stomach. For this reason, the conventional receiving apparatus poses the problem that the radio signal is liable to be received from the capsule endoscope in the esophagus through a receiving antenna distant from the esophagus among the plurality of receiving antennas dispersively arranged outside the subject, and that the image data in the esophagus of the subject is liable to be acquired based on the received radio signal having a weak received field strength, so that it is difficult to obtain image data in the esophagus of the subject in a satisfactory state low in noises.

This invention has been achieved in view of the situation described above, and an object thereof is to provide a receiving apparatus capable of sequentially receiving, with a satisfactory sensitivity, radio signals sequentially transmitted in a short period of time before a body-insertable device such as a capsule endoscope swallowed into a subject reaches his/her stomach and acquiring, in a satisfactory state, image data in the subject picked up by the capsule endoscope, and an in-vivo information acquiring system using the receiving apparatus.

Means for Solving Problem

A receiving apparatus according to one aspect of the present invention has a plurality of receiving antennas that receives a radio signal from a mobile unit movable in a subject, and acquires data on the interior of the subject based on the radio signal received through any one of the plurality of receiving antennas. The apparatus also includes a specified receiving antenna that receives the radio signal from the mobile unit until a predetermined portion in the subject is reached; a switching controller that performs either an antenna switching control operation in an initial mode for switching the receiving antenna that receives the radio signal to the specified receiving antenna to maintain the state or an antenna switching control operation in a normal mode for switching to any one of the plurality of receiving antennas; a determining unit that determines whether the mobile unit has reached the predetermined portion in the subject or not; and a mode switching unit that instructs the switching controller to perform the antenna switching control operation in the initial mode, the mode switching unit instructing the switching controller to perform the antenna switching control operation by switching the initial mode to the normal mode, when the determining unit determines that the mobile unit has reached the predetermined portion in the subject.

The receiving apparatus may further include a detector that detects information on the data included in the radio signal. In the receiving apparatus, the determining unit may determine whether the mobile unit has reached the predetermined portion in the subject or not, based on the information on the data detected by the detector.

In the receiving apparatus, the data may be image data imaged by the mobile unit.

In the receiving apparatus, the information on the data may be one of brightness information, chromaticity information, and an imaging interval of the data.

The receiving apparatus may further include a time counting unit that measures time elapsed after switching to the specified receiving antenna and notifies the determining unit of the elapsed time. In the receiving apparatus, the determining unit may determine whether the mobile unit has reached the predetermined portion in the subject or not, based on the elapsed time measured by the time counting unit.

In the receiving apparatus the predetermined portion may be the stomach of the subject.

The receiving apparatus may further include a received strength detector that detects a received electric-field strength of the radio signal. In the receiving apparatus, the switching controller may perform the antenna switching control operation in the normal mode for switching to the receiving antenna having the highest received electric-field strength of the radio signal among at least the plurality of receiving antennas.

An in-vivo information acquiring system according to another aspect of the present invention includes a capsule endoscope that is introduced into a subject to output a radio signal including image data picked up while moving in the subject; and the receiving apparatus according to the present invention.

An in-vivo information acquiring system according to still another aspect of the present invention includes a capsule endoscope that is introduced into a subject to output a radio signal including image data picked up in the subject; a receiving apparatus that has a plurality of receiving antennas including a specified receiving antenna for receiving a radio signal from the capsule endoscope until a predetermined portion in the subject is reached, and acquires the image data based on the radio signal received through the receiving antenna switched to among the plurality of receiving antennas; and a monitor device that is connected to the receiving apparatus to detect information on the image data acquired through the receiving apparatus while at the same time monitoring and displaying the image data. The receiving apparatus switches the receiving antenna for receiving the radio signal to the specified one among the plurality of receiving antennas, and based on the information on the image data detected by the monitor device, determines whether the capsule endoscope has reached the predetermined portion in the subject or not, the specified receiving antenna being switched to the remaining ones of the plurality of receiving antennas upon determination that the predetermined portion in the subject has been reached.

In the in-vivo information acquiring system, the information on the image data may be brightness information or chromaticity information of the image data.

An in-vivo information acquiring system according to still another aspect of the present invention includes a capsule endoscope that is introduced into a subject to sequentially detect a current position in the subject, and before a predetermined portion in the subject is detected as the current position, images the interior of the subject at predetermined intervals, the interior of the subject being imaged at longer than the predetermined intervals upon detection of the predetermined portion in the subject as the current position, followed by outputting a radio signal including the image data obtained; and a receiving apparatus that has a plurality of receiving antennas including a specified receiving antenna for receiving a radio signal from the capsule endoscope until a predetermined portion in the subject is reached, and acquires the image data based on the radio signal received through the receiving antenna switched to among the plurality of receiving antennas. The receiving apparatus switches the receiving antenna for receiving the radio signal to the specified one among the plurality of receiving antennas, detects the imaging intervals of the image data, and based on the imaging intervals of the image data thus detected, determines whether the capsule endoscope has reached the predetermined portion in the subject or not, the specified receiving antenna being switched to the remaining ones of the plurality of receiving antennas upon determination that the predetermined portion in the subject has been reached.

An in-vivo information acquiring system according to still another aspect of the present invention includes a capsule endoscope that is introduced into a subject to measure a pH value at a current position in a subject while at the same time imaging the interior of the subject at the current position, and outputs a radio signal including image data obtained and the pH value; and a receiving apparatus that has a plurality of receiving antennas including a specified receiving antenna for receiving a radio signal from the capsule endoscope until a predetermined portion in the subject is reached, and acquires the image data based on the radio signal received through the receiving antenna switched to among the plurality of receiving antennas. The receiving apparatus switches the receiving antenna for receiving the radio signal to the specified one of the plurality of receiving antennas, detects the pH value based on the radio signal, and based on the pH value thus detected, determines whether the capsule endoscope has reached the predetermined portion in the subject or not, the specified receiving antenna being switched to the remaining ones of the plurality of receiving antennas upon determination that the predetermined portion in the subject has been reached.

In the in-vivo information acquiring system, the predetermined portion in the subject may be the stomach of the subject.

In the in-vivo information acquiring system, the receiving apparatus may detect a received electric-field strength of the radio signal, and upon determination that the predetermined portion in the subject has been reached, may switch to the receiving antenna having the highest received electric-field strength of the radio signal among the plurality of receiving antennas.

Effect of the Invention

According to this invention, the radio signal from the capsule endoscope as being a body-insertable device before reaching a predetermined portion of the subject can be received with a high sensitivity through a specified receiving antenna. In addition, the radio signal from the capsule endoscope after reaching the predetermined portion can be received with a high sensitivity through any one of the plurality of receiving antennas. Consequently, the radio signal from the capsule endoscope can be received with a satisfactory sensitivity from the receiving antenna having the highest received electric field strength among the plurality of receiving antennas during the period after the capsule endoscope is swallowed into the subject before it is discharged out of the body. Thus, the capsule endoscope can certainly acquire image data in a satisfactory state in the subject including image data in the esophagus picked up while passing through it in a period of time as short as about 4 seconds.

EXPLANATIONS OF LETTERS OR NUMERALS

Figure 1:
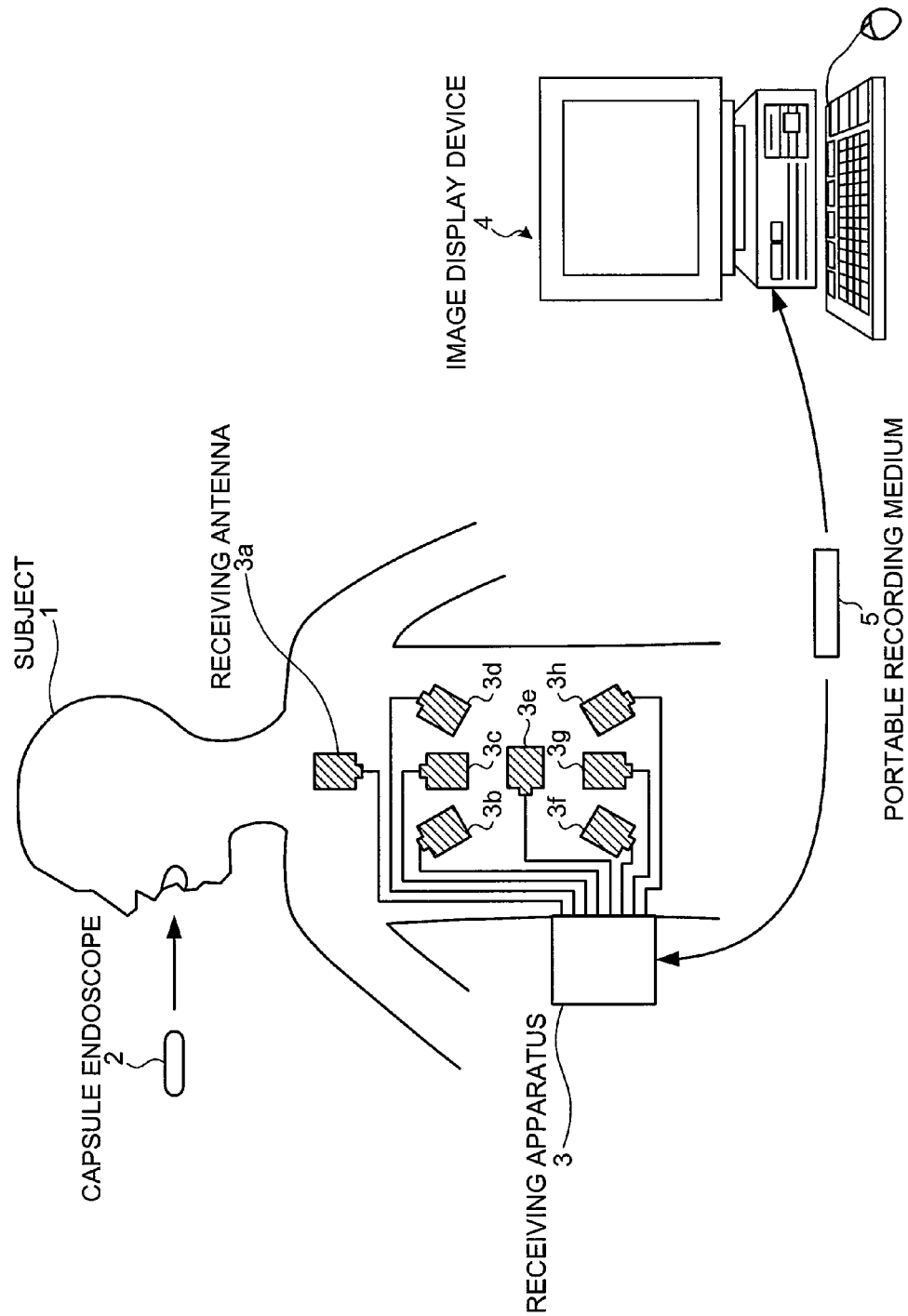
FIG. 1 is a schematic diagram schematically showing an example of the configuration of an in-vivo information acquiring system according to a first embodiment of the invention.

1 Subject
2 Capsule endoscope
3, 8 Receiving apparatus
3a to 3h Receiving antenna
4 Image display device
5 Portable recording medium
6 Monitor device
7 Cable
21 Illuminating unit
22 Illuminating unit driving circuit
23 Imaging unit
24 Imaging unit driving circuit
25 Image processor
26 Transmitting circuit
27 Transmitting antenna
28 Control unit
29 Power supply unit
30 Antenna switching unit
31, 81 Receiving circuit
32 Received strength detector
33 Switching controller
34 Image processor
34a Signal detector
35 Storage unit
36 Input unit
37, 87 Display unit
38, 88 Control unit
38a Arrival determining unit
38b, 88b Mode switching unit
39 Power supply unit
61 Receiving antenna
62 Receiving circuit
63 Image processor
63a Signal detector
64 Communication I/F
65 Connection detector
66 Input unit
67 Display unit
68 Control unit
69 Power supply unit
82 Communication I/F
83 Connection detector
84 Image generator
120 Capsule endoscope
121 Sensor unit
128 Control unit
128a Mode switching unit
130 Receiving apparatus
134 Image processor
134a Imaging interval detector
138 Control unit
138a Arrival determining unit
220 Capsule endoscope
221 pH measuring unit
225 Image processor
225a Superimposing processor
228 Control unit
230 Receiving apparatus
234 Image processor
234a pH value detector
238 Control unit 238a Arrival determining unit
330 Receiving apparatus
334 Image processor
338 Control unit
338a Arrival determining unit
338c Time count processor

BEST MODE(S) FOR CARRYING OUT THE INVENTION

Preferred embodiments of a receiving apparatus according to the invention and an in-vivo information acquiring system using the receiving apparatus will be explained in detail below with reference to the drawings. Nevertheless, the invention is not limited to the embodiments.

First Embodiment

FIG. 1 is a schematic diagram schematically showing an example of the configuration of an in-vivo information acquiring system according to a first embodiment of the invention. As shown in FIG. 1, the in-vivo information acquiring system according to the first embodiment comprises a capsule endoscope 2 for imaging the interior of a subject 1 while moving along a passage in the subject 1, a receiving apparatus 3 for receiving a radio signal including image data picked by the capsule endoscope 2, an image display device 4 for displaying an image in the subject 1 based on the image data picked up by the capsule endoscope 2, and a portable recording medium 5 for delivering the data between the receiving apparatus 3 and the image display device 4.

The capsule endoscope 2 serves as a body-insertable device, has a capsule-type casing structure capable of being easily introduced into the subject 1, and has both an imaging function to image the interior of the subject 1 and a radio communication function to transmit image data obtained by imaging the interior of the subject 1 to the external receiving apparatus 3. Specifically, the capsule endoscope 2 is swallowed from the mouth of the subject 1, and after passing through the esophagus in the subject 1 in about 4 seconds, proceeds through the body cavity by the vermiculation of the alimentary canals such as the stomach and the small intestine. At the same time, the capsule endoscope 2 images the interior of the body cavity of the subject 1 sequentially, and transmits the radio signal including the image data on the interior of the subject 1 thus obtained to the receiving apparatus 3 sequentially.

The receiving apparatus 3 is for receiving the radio signal from the capsule endoscope 2 introduced into the subject 1 and acquiring the image data due to the capsule endoscope 2 based on the radio signal. Specifically, the receiving apparatus 3 includes a plurality of receiving antennas 3a to 3h for receiving a radio signal from the capsule endoscope 2. The radio signal received from the capsule endoscope 2 through any one of the receiving antennas 3a to 3h is demodulated into an image signal, and based on the image signal thus obtained, image data from the capsule endoscope 2 is acquired. In this case, the receiving apparatus 3 stores, as required, the image data due to the capsule endoscope 2, in the portable recording medium 5 inserted removably therein.

The receiving antennas 3a to 3h are implemented by using, for example, loop antennas, and receive a radio signal transmitted by the capsule endoscope 2. Specifically, among the plurality of receiving antennas 3a to 3h, the receiving antenna 3a, as shown in FIG. 1, is a specified receiving antenna arranged at a specified position outside the subject 1 such as in the neighborhood of the esophagus on the body surface of the subject 1, and receives a radio signal from the capsule endoscope d2 after deglutition into the subject 1 and passing through the esophagus before reaching the stomach. In this case, the receiving antenna 3a, as compared with the remaining antennas 3b to 3h, is nearest to the esophagus of the subject 1 among the plurality of receiving antennas 3a to 3h. Therefore, the receiving antenna 3a receives, from the capsule endoscope 2, a radio signal having a higher received field strength than the remaining receiving antennas 3b to 3h during the period before the capsule endoscope 2 reaches the stomach after being swallowed.

The remaining receiving antennas 3b to 3g, on the other hand, are dispersively arranged at predetermined positions on the surface of the subject 1 other than the specified position at which the receiving antenna 3a has been arranged, or as shown in FIG. 1, for example, at the positions corresponding to the passage (specifically, the passage including and after the stomach) of the capsule endoscope 2. One of the remaining receiving antennas 3b to 3g can receive a radio signal of a high received field strength from the capsule endoscope 2 during the period after the arrival of the capsule endoscope 2 at the stomach before the capsule endoscope 2 is discharged out of the body of the subject 1.

The receiving antennas 3a to 3h may be arranged at predetermined positions of a jacket worn by the subject 1. With the subject 1 wearing the jacket, the receiving antenna 3a is arranged at a specified position (in the neighborhood of the esophagus, for example) on the body surface of the subject 1, while the remaining receiving antennas 3b to 3h are arranged dispersively at predetermined positions on the body surface of the subject 1 other than the specified position. Also, a plurality of receiving antennas including at least one specified receiving antenna and at least one remaining receiving antenna can be arranged at the specified position, etc. on the subject 1. In this case, the number of the receiving antennas thus arranged is not specifically limited to 8.

The image display device 4 is for displaying an image in the subject 1 picked up by the capsule endoscope 2, and displays an image of the organs or the like in the subject 1 (i.e. an image picked up by the capsule endoscope 2) based on image data obtained through the portable recording medium 5. Also, the image display device 4 has a processing function to diagnose the subject 1 by a doctor or a nurse observing the image of the organs, etc. in the subject 1 through the capsule endoscope 2.

The portable recording medium 5 is for receiving and delivering data between the receiving apparatus 3 and the image display device 4, and constitutes, for example, a portable recording medium such as CompactFlash®. The portable recording medium 5 is removably mounted in the receiving apparatus 3 and the image display device 4, and has such a structure that data can be output and recorded at the time of insertion into the receiving apparatus 3 and the image display device 4. Specifically, assume that the portable recording medium 5 is inserted in the receiving apparatus 3. In this case, image data, etc. acquired by the receiving apparatus 3 from the capsule endoscope 2 are sequentially accumulated in the portable recording medium 5. Also, the portable recording medium 5, after the capsule endoscope 2 is discharged from the subject 1, is recovered from the receiving apparatus 3 and inserted into the image display device 4. In this case, the image display device 4 can retrieve various data such as the image data on the interior of the subject 1 stored in the portable recording medium 5 thus inserted.

By receiving and delivering the data between the receiving apparatus 3 and the image display device 4 using the portable recording medium 5, the subject 1, unlike in the case where the receiving apparatus 3 and the image display device 4 are connected by wire such as a cable to each other, can freely behave carrying the receiving apparatus 3 even while the capsule endoscope 2 moves in the subject 1.

Figure 2:
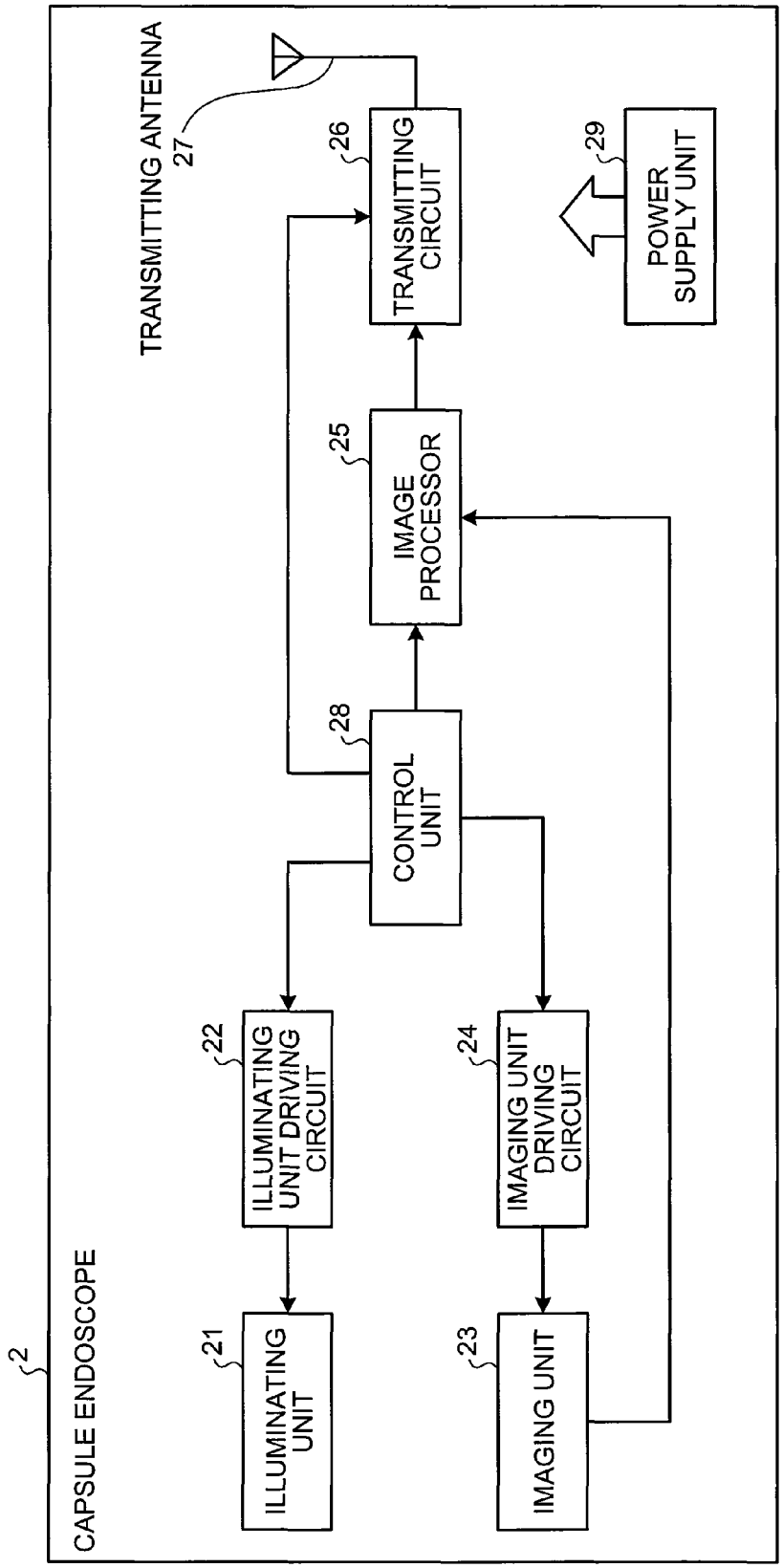
FIG. 2 is a block diagram schematically showing an example of the configuration of a capsule endoscope configuring a part of the in-vivo information acquiring system according to the first embodiment of the invention.

Next, the configuration of the capsule endoscope 2 for use in the in-vivo information acquiring system according to the first embodiment will be explained. FIG. 2 is a block diagram schematically showing an example of the configuration of the capsule endoscope 2. As shown in FIG. 2, the capsule endoscope 2 includes an illuminating unit 21 for illuminating an imaging area at the time of imaging the interior of the subject 1, an illuminating unit driving circuit 22 for controlling the drive of the illuminating unit 21, an imaging unit 23 for picking up a reflected light image from the area illuminated by the illuminating unit 21, and an imaging unit driving circuit 24 for controlling the drive of the imaging unit 23. Also, the capsule endoscope 2 includes an image processor 25 for generating an image signal including image data picked up by the imaging unit 23, a transmitting circuit 26 for generating a radio signal by modulating the image signal generated by the image processor 25, and a transmitting antenna 27 for outputting the radio signal generated by the transmitting circuit 26 outside. Further, the capsule endoscope 2 includes a control unit 28 for controlling the drive of each component part of the capsule endoscope 2 and a power supply unit 29 for supplying a driving power to each component part of the capsule endoscope 2.

The illuminating unit 21 is implemented by use of a light emitting element such as an LED, and illuminates by outputting the illuminating light on the area imaged by the imaging unit 23. The imaging unit 23 is implemented by use of an imaging element such as a CCD or a CMOS, and receives the reflected light from the area (i.e. the imaging area) illuminated by the illuminating unit 21 so as to image the imaging area (for example, the interior of the subject 1). The imaging unit 23 outputs to the image processor 25 the image data obtained by this imaging process. The control unit 28 controls the illuminating unit driving circuit 22 and the imaging unit driving circuit 24 in such a manner as to establish synchronism between the illumination timing of the imaging area by the illuminating unit 21 and the imaging timing of the imaging area by the imaging unit 23.

The image processor 25 generates an image signal including the image data picked up by the imaging unit 23. In this case, the image processor 25 generates the image signal without compressing the image data. Specifically, the image processor 25 generates an image signal including image data not compressed and parameters such as preset white balance data. The image processor 5 transmits the image signal thus generated to the transmitting circuit 26.

The transmitting circuit 26 executes a predetermined modulation process and power amplification process on the image signal generated by the image processor 25 and generates a radio signal obtained by modulating the image signal. The radio signal contains the image data picked up by the imaging unit 23 and the parameters such as the white balance data. The transmitting circuit 26 outputs the radio signal thus generated to the transmitting antenna 27. The transmitting antenna 27 outputs the radio signal input from the transmitting circuit 26 to an external part. In this case, the capsule endoscope 2 outputs the radio signal including at least the image data picked up by the imaging unit 23, for example, the image data picked up on the interior of the subject 1 to an external part.

Figure 3:
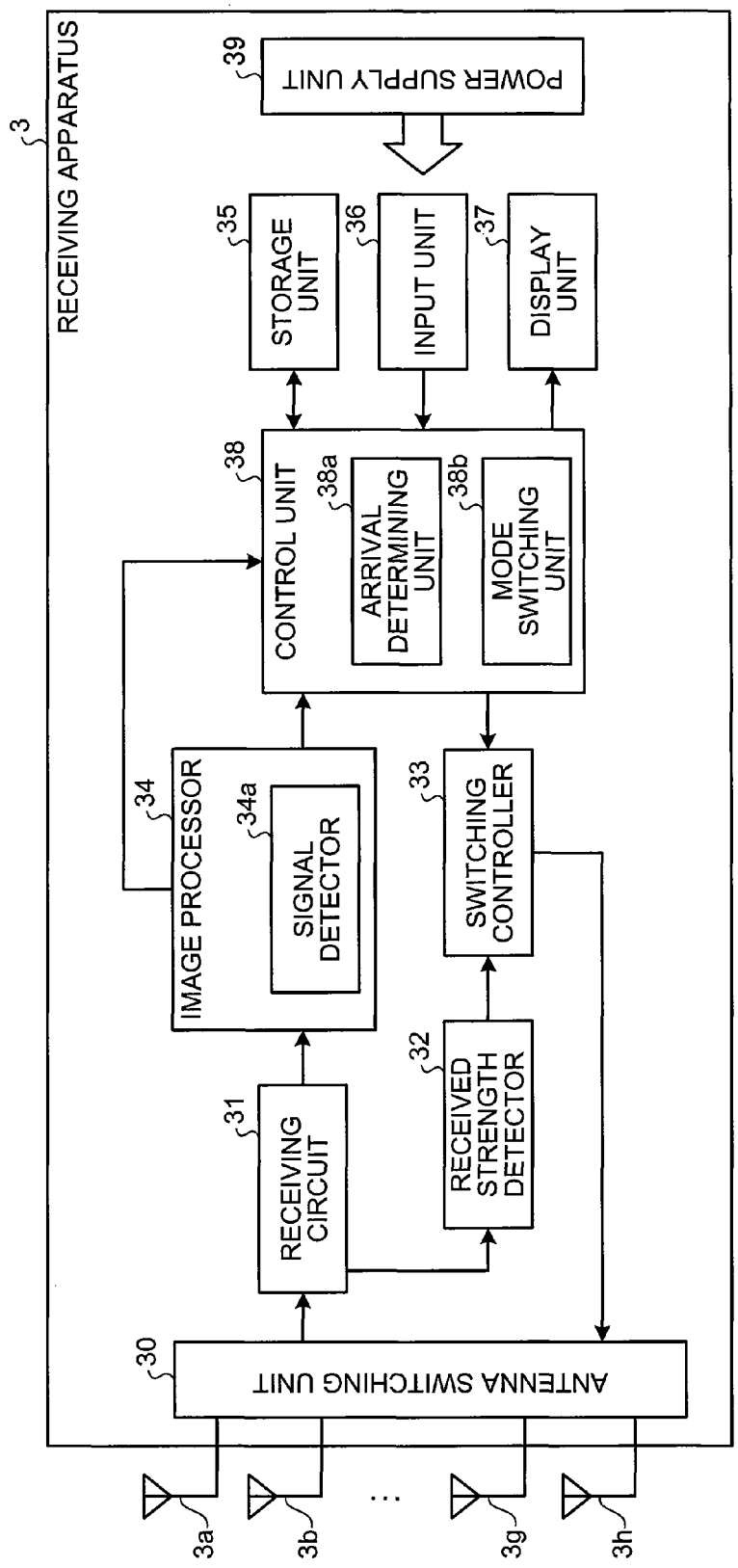
FIG. 3 is a block diagram schematically showing an example of the configuration of a receiving apparatus according the first embodiment of the invention.

Next, the configuration of the receiving apparatus 3 according to the first embodiment of the invention will be explained. FIG. 3 is a block diagram schematically showing an example of the configuration of the receiving apparatus 3 according to the first embodiment of the invention. As shown in FIG. 3, the receiving apparatus 3 is connected with a plurality of receiving antennas 3a to 3h, and includes an antenna switching unit 30 for switching to a receiving antenna suitable for receiving a radio signal among the receiving antennas 3a to 3h, a receiving circuit 31 for demodulating a radio signal received through one of the receiving antennas 3a to 3h into an image signal, a received strength detector 32 for detecting a received field strength of the radio signal based on a baseband signal demodulated by the receiving circuit 31, and a switching controller 33 for controlling the antenna switching operation of the antenna switching unit 30 based on the received field strength detected by the received strength detector 32. Also, the receiving apparatus 3 includes an image processor 34 for generating image data due to the capsule endoscope 2 based on the image signal demodulated by the receiving circuit 31, a storage unit 35 for storing the image data, etc. generated by the image processor 34, an input unit 36 for inputting instruction information for giving an instruction on various operations of the receiving apparatus 3, and a display unit 37 for displaying information on the subject 1 including the image of the subject 1. Further, the receiving apparatus 3 includes a control unit 38 for controlling the drive of each component part of the receiving apparatus 3 and a power supply unit 39 for supplying a driving power to each component part of the receiving apparatus 3.

The antenna switching unit 30 functions to perform the antenna switching operation for electrically connecting the switched one of the plurality of receiving antennas 3a to 3h and the receiving circuit 31. Specifically, the antenna switching unit 30 performs the antenna switching operation based on any one of two control modes by the switching controller 33, and electrically connects the receiving circuit 31 with any one of the receiving antennas 3a to 3h suitable for receiving the radio signal from the capsule endoscope 2. More specifically, the antenna switching unit 30, based on the control operation in an initial mode of the switching controller 33, performs the antenna switching operation (specified antenna switching operation) to switch to the receiving antenna 3a among the plurality of receiving antennas 3a to 3h thereby to connect the receiving antenna 3a and the receiving circuit 31 electrically while at the same time maintaining this connection, and the receiving antenna for receiving the radio signal from the capsule endoscope 2 is fixed on the receiving antenna 3a. The antenna switching unit 30, on the other hand, based on the control operation in a normal mode of the switching controller 33 switched from the initial mode, performs the antenna switching operation (normal antenna switching operation) for electrically connecting the receiving circuit 31 with the sequentially switched one of the remaining receiving antennas 3b to 3h. The antenna switching unit 30 outputs, to the receiving circuit 31, the radio signal received from the capsule endoscope 2 through the selected one of the receiving antennas 3a to 3h.

The receiving circuit 31 is for demodulating a radio signal input from the antenna switching unit 30 to a baseband signal. Specifically, the receiving circuit 31 executes the demodulating process on a radio signal input from the antenna switching unit 30 thereby to demodulate the radio signal into an image signal constituting a baseband signal. The image signal is a baseband signal including at least the image data picked up by the capsule endoscope 2. The receiving circuit 31 outputs the baseband signal (i.e. the image signal) thus obtained to the received strength detector 32 and the image processor 34.

The received strength detector 32 is for detecting a received electric-field strength of a radio signal received from the capsule endoscope 2 through any one of the receiving antennas 3a to 3h. Specifically, the received strength detector 32, based on the baseband signal demodulated by the receiving circuit 31, detects a received electric-field strength of a radio signal corresponding to the baseband signal, and outputs the signal indicating the received electric-field strength, such as a received signal strength indicator (RSSI), to the switching controller 33.

The switching controller 33 is for controlling the specified antenna switching operation and the normal antenna switching operation by the antenna switching unit 30. Specifically, the switching controller 33 has two control modes for controlling the drive of the antenna switching unit 30. These two control modes include an initial mode for controlling the antenna switching unit 30 in such a manner as to perform the specified antenna switching operation described above and a normal mode for controlling the antenna switching unit 30 in such a manner as to perform the normal antenna switching operation described above.

In the control operation of the initial mode, the switching controller 33 switches to and maintains a state in which the receiving antenna 3a constituting the specified receiving antenna described and the receiving circuit 31 are electrically connected with each other (initial state of the antenna switching unit 30), and fixes the receiving antenna for receiving the radio signal from the capsule endoscope 2, on the receiving antenna 3a. In the control operation of the normal mode, on the other hand, the switching controller 33 sequentially switches to a receiving antenna suitable for receiving the radio signal among the remaining receiving antennas 3b to 3h, while at the same time controlling the antenna switching unit 30 in such a manner as to connect the switched receiving antenna and the receiving circuit 31 electrically to each other. In this case, the switching controller 33, based on the signal (RSSI signal, for example) indicating the received electric-field strength input from the received strength detector 32, selects a receiving antenna associated with the highest received electric-field strength of the radio signal among the remaining receiving antennas 3b to 3h, and controls the antenna switching unit 30 in such a manner as to connect the selected receiving antenna and the receiving circuit 31 electrically to each other.

The image processor 34 is for generating image data included in a radio signal received from the capsule endoscope 2 through any one of the plurality of receiving antennas 3a to 3h. Specifically, the image processor 34 executes a predetermined image processing operation on an image signal demodulated by the receiving circuit 31, and generates image data due to the capsule endoscope 2 based on the image signal. The image processor 34 outputs the image data thus obtained to the control unit 38.

Also, the image processor 34 includes a signal detector 34a for detecting information on image data based on an image signal. The signal detector 34a, based on an image signal demodulated by the receiving circuit 31, detects information on image data, such as brightness information on the image data, included in the image signal. In this case, the signal detector 34a, based on this image signal, detects a brightness signal corresponding to the brightness information of the image data and outputs the detected brightness signal to the control unit 38.

The storage unit 35, into which the portable recording medium 5 can be replaceably inserted, sequentially stores, in the portable recording medium 5, data instructed by the control unit 38 to be stored store, for example, the image data generated by the image processor 34. The storage unit 35 may be configured of a memory IC such as a RAM or a flash memory to accumulate various information such as the image data in itself.

The input unit 36 is implemented by using an input button for inputting instruction information instructing the control unit 38. In accordance with the input operation of the user, various instruction information such as an instruction to display information (name of a patient, patient ID, etc.) of the subject 1 on the display unit 37 are input to the control unit 38. The display unit 37 is implemented by use of a thin display such as a liquid crystal display device or an organic EL panel, and displays information instructed by the control unit 38 to be displayed, such as the information on the subject 1 or the image of the subject 1. Incidentally, the display unit 37 may have an information input function such as a touch panel, and the instruction information may be input to the control unit 38 in place of the input unit 36. In this case, the receiving apparatus 3 may have not the input unit 36.

The control unit 38 is implemented by using a CPU for executing a processing program, a ROM having stored therein the processing program, etc. in advance, and a RAM for storing operation parameters or information input to the control unit 38. The control unit 38 controls the drive of each component part of the receiving apparatus 3. In this case, the control unit 38 controls information input/output to and from each component part while at the same time controlling the operation to store and read the data in and from the storage unit 35 (specifically, the portable recording medium 5) and the display operation on the display unit 37. The control unit 38 executes various processes based on the instruction information input by the input unit 36.

Also, the control unit 38 controls the switching controller 33 to switch the control mode of the switching controller 33 described above to the initial mode or the normal mode. Specifically, the control unit 38 instructs the switching controller 33 to control the specified antenna switching operation in the initial mode during the period before the capsule endoscope 2 swallowed from the mouth of the subject 1 reaches a predetermined portion such as the stomach in the subject 1. The control unit 38, on the other hand, instructs the switching controller 33 to control the normal antenna switching operation in the normal mode during the period before the capsule endoscope 2 is discharged out of the body of the subject 1 after reaching the stomach of the subject 1. The control unit 38 includes an arrival determining unit 38a for determining whether the capsule endoscope 2 introduced into the subject 1 has reached a predetermined portion (such as the stomach) of the subject 1 or not and a mode switching unit 38b for switching the control mode of the switching controller 33 to the initial mode or the normal mode.

The arrival determining unit 38a, based on the information on the image data detected by the signal detector 34a, determines whether the capsule endoscope 2 in the subject 1 has reached a predetermined portion such as the stomach of the subject 1 or not. In this case, the arrival determining unit 38a acquires the brightness information of the image data based on the brightness signal detected by the signal detector 34a, for example, and based on the change in the brightness information such as a brightness value of the image data, determines whether the capsule endoscope 2 has reached the stomach of the subject 1 or not.

In the case where the on/off state of a power supply switch (not shown) arranged in the power supply unit 39 is turned on, i.e. in the case where the driving power is supplied by the power supply unit 39, the mode switching unit 38b switches the control mode of the switching controller 33 to the initial mode described above by using, as a trigger, the fact that the driving power has begun to be supplied from the power supply unit 39. In the case where the arrival determining unit 38a determines that the capsule endoscope 2 has reached a predetermined portion (such as the stomach) of the subject 1, on the other hand, the mode switching unit 38b switches the control mode of the switching controller 33 to the normal mode described above by using, as a trigger, the arrival determination result of the arrival determining unit 38a.

The power supply unit 39, having a power supply switch (not shown) for switching the on/off state of the driving power supply, supplies the driving power to each component part of the receiving apparatus 3 in the case where the power supply switch is turned on. Incidentally, a dry battery, a lithium-ion secondary battery or a nickel hydrogen battery, etc. is used, for example, as the power supply of the power supply unit 39. Also, the power supply unit 39 may be of charged type.

Figure 4:
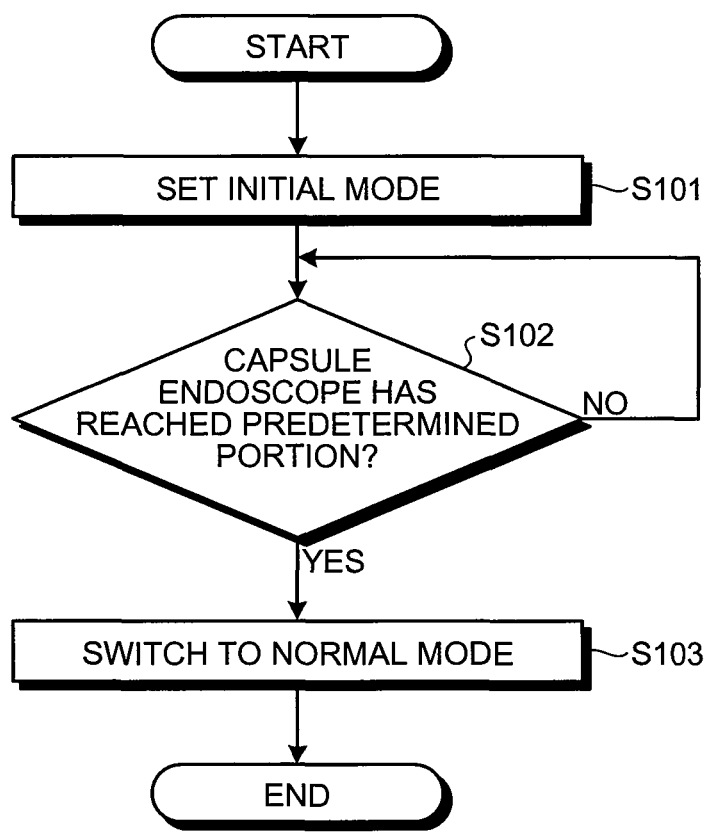
FIG. 4 is a flowchart for explaining the procedures for switching a control mode of a switching controller.

Next, the operation of the control unit 38 to switch the control mode of the switching controller 33 to the initial mode or the normal mode described above will be explained. FIG. 4 is a flowchart for explaining the procedures of the control unit 38 to switch the control mode of the switching controller 33. In FIG. 4, first, assume that the power supply unit 39 begins to supply the driving power by the switching operation of the power supply switch. The control unit 38 instructs the switching controller 33 to set the control mode for controlling the drive of the antenna switching unit 30 to the initial mode described above (step S101). In this case, the mode switching unit 38b switches the control mode of the switching controller 33 to the initial mode by using, as a trigger, the fact that the power supply unit 39 has begun to supply the driving power. Based on this control operation of the control unit 38, the switching controller 33 controls the drive of the antenna switching unit 30 in the initial mode so as to set the antenna switching unit 30 in the initial mode described above, and controls the specified antenna switching operation to maintain the state in which the receiving antenna 3a and the receiving circuit 31 are electrically connected to each other.

Next, the control unit 38 determines whether the capsule endoscope 2 introduced into the subject 1 has reached a predetermined portion of the subject 1 or not (step S102), and in accordance with the arrival determination result of the capsule endoscope 2, switches the control mode of the switching controller 33. In this case, the arrival determining unit 38a acquires brightness information of the image data based on the brightness signal detected by the signal detector 34a, and determines whether the capsule endoscope 2 has reached the predetermined portion of the subject 1 or not, based on the change in the brightness information thus obtained. In the case where the arrival determining unit 38a fails to determine that the capsule endoscope 2 has reached the predetermined portion of the subject 1 (NO in step S102), the control unit 38 repeats the process of step S102 and monitors to check to see whether the capsule endoscope 2 has reached the predetermined portion of the subject 1 or not.

In the case where the arrival determining unit 38a determines that the capsule endoscope 2 has reached a predetermined portion of the subject 1 (YES in step S102), on the other hand, the control unit 38 controls the switching controller 33 to switch the control mode of the switching controller 33 from the initial mode to the normal mode described above (step S103). In this case, the mode switching unit 38b switches the control mode of the switching controller 33 from the initial mode to the normal mode described above by using, as a trigger, the determination by the arrival determining unit 38a that the capsule endoscope 2 has reached the predetermined portion of the subject 1. Based on the control operation of the control unit 38, the switching controller 33 switches the control mode from the initial mode to the normal mode while at the same time controlling both the drive of the antenna switching unit 30 in the normal mode and the normal antenna switching operation for electrically connecting any one of the receiving antennas 3b to 3h and the receiving circuit 31 to each other.

Figure 5:
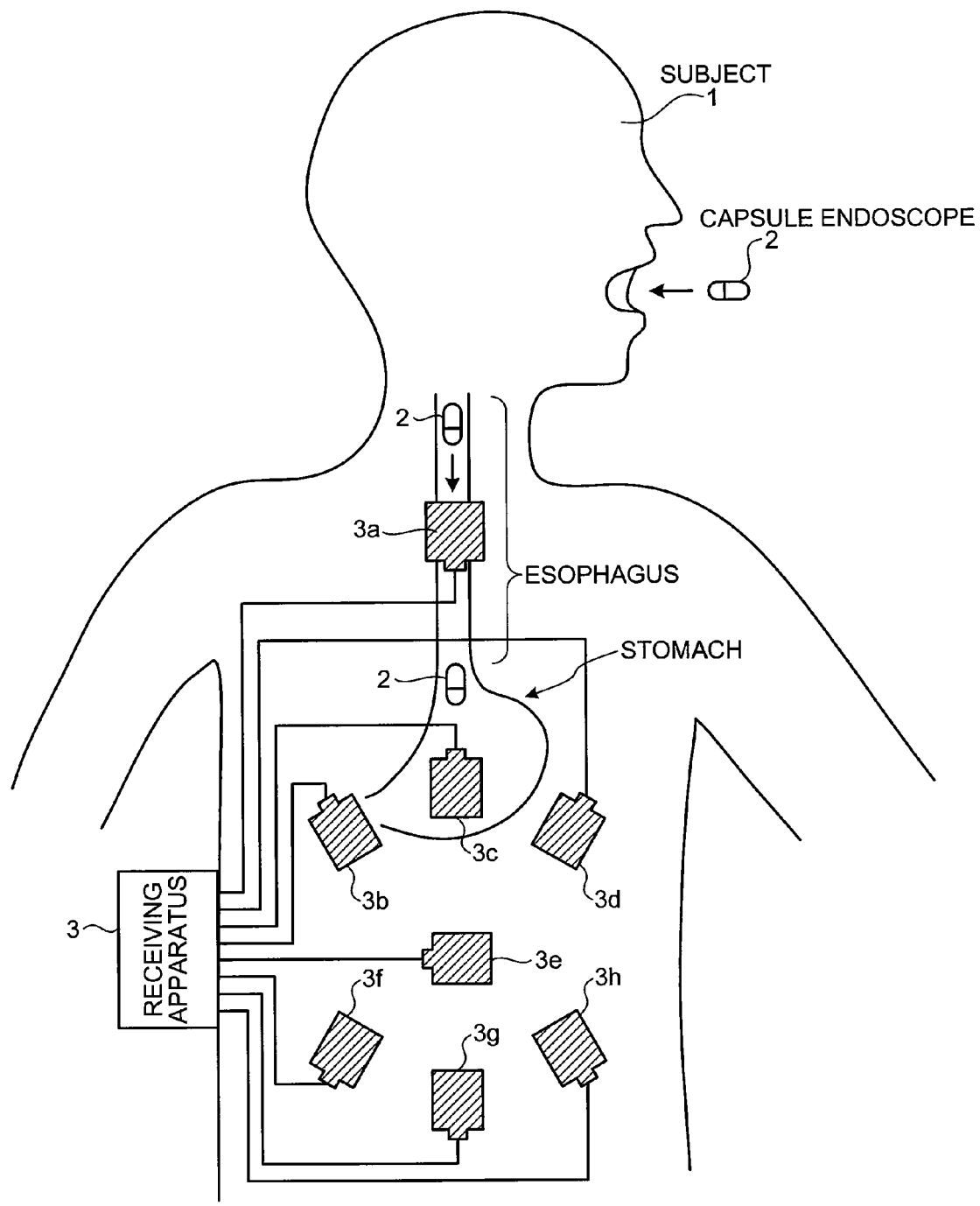
FIG. 5 is a schematic diagram for specifically explaining the operation of a control unit to switch the control mode of the switching controller to an initial mode or normal mode.

Now, taking the case in which the predetermined portion of the subject 1 described above is the stomach as an example, the operation of the control unit 38 for setting the control mode of the switching controller 33 to the initial mode and then switching the initial mode to the normal mode will be specifically explained. FIG. 5 is a schematic diagram for specifically explaining the operation of the control unit 38 to switch the control mode of the switching controller 33 to the initial mode or the normal mode described above.

As shown in FIG. 5, first, the receiving apparatus 3 is so operated that the power supply switch of the power supply unit 39 is turned on, and immediately before or after this operation, the capsule endoscope 2 is swallowed from the mouth of the subject 1. Under this condition, the antenna switching unit 30 is controlled by the switching controller 33 in the initial mode, so that the receiving antenna 3a and the receiving unit 31 are electrically connected to each other and this connected state is maintained. In this case, the capsule endoscope 2 that has been swallowed into the subject 1 moves from the mouth to the interior of the subject 1 and passes through the esophagus of the subject 1 in as short a time as about 4 seconds. At the same time, the capsule endoscope 2 picks up image data in the subject 1, and sequentially outputs a radio signal including the image data thus obtained. The radio signal from the capsule endoscope 2 is received by the receiving apparatus 3 through the receiving antenna 3a arranged on the body surface of the subject 1 in the neighborhood of the esophagus. This transmission and reception of the radio signal is maintained until the capsule endoscope 2 swallowed by the subject 1 reaches his/her stomach.

Thereafter, the capsule endoscope 2 that has passed through the esophagus of the subject 1 outputs the radio signal including the image data of the stomach of the subject 1 picked up while at the same time reaching the stomach of the subject 1. The radio signal including the image data on the stomach of the subject 1 thus picked up is received by the receiving apparatus 3 through the receiving antenna 3a. In this case, the receiving circuit 31 demodulates the radio signal received through the receiving antenna 3a into an image signal, and the image processor 34 generates image data of the stomach of the subject 1 based on the image signal. Also, the signal detector 34a detects a brightness signal based on this image signal, and the arrival determining unit 38a acquires brightness information of the picked-up image data of the stomach of the subject 1 based on the brightness signal detected by the signal detector 34a. The arrival determining unit 38a determines that the capsule endoscope 2 has reached the stomach of the subject 1, based on the change in the brightness information of the image data corresponding to the arrival of the capsule endoscope 2 at the stomach through the esophagus of the subject 1.

Upon determination by the arrival determining unit 38a that the capsule endoscope 2 has reached the stomach of the subject 1, the mode switching unit 38b switches the control mode of the switching controller 33 from the initial mode to the normal mode. In this case, the antenna switching unit 30 is controlled by the switching controller 33 in the normal mode, and performs the normal antenna switching operation to electrically connect the receiving circuit 31 and any one of the remaining receiving antennas 3b to 3h dispersively arranged on the body surface of the subject 1 corresponding to the passage (such as the, small intestine and large intestine) of the capsule endoscope 2 in the stomach and the subsequent organs of the subject 1. In other words, after the capsule endoscope 2 swallowed by the subject 1 reaches the stomach of the subject 1, the radio signal from the capsule endoscope d2 is received by the receiving apparatus 3 through the receiving antenna having the highest received field strength among the remaining receiving antennas 3b to 3h.

In the receiving apparatus 3, the receiving antenna for receiving the radio signal from the capsule endoscope 2 swallowed from the mouth of the subject 1 and yet to reach the stomach is fixed on the receiving antenna 3a until it reaches the stomach. Thereafter, the receiving antenna for receiving the radio signal from the capsule endoscope 2 that has reached the stomach of the subject 1 is switched to any one of the remaining receiving antennas 3b to 3h before the capsule endoscope 2 is discharged. The receiving apparatus 3, therefore, can receive the radio signal from the capsule endoscope 2 with a satisfactory sensitivity through the receiving antenna highest in received field strength among the plurality of receiving antennas 3a to 3h during the period from the time when the capsule endoscope 2 is swallowed into the subject 1 until it is discharged out of the body. As a result, the satisfactory image data (i.e. the image data in good state with very small noises) on the interior of the subject 1 including the image data in the esophagus imaged by the capsule endoscope 2 while passing through the esophagus within a time as short as 4 seconds can be certainly acquired.

According to the first embodiment of the invention, the brightness information of the image data is detected as the information on the image data to determine whether the capsule endoscope 2 has reached a predetermined portion of the subject 1 or not. Nevertheless, the invention is not limited to this configuration, but color information of the image data may be detected in place of the brightness information. In this case, the signal detector 34a detects a chromaticity signal corresponding to color information of the image data based on the image signal, and outputs the detected chromaticity signal to the control unit 38. The arrival determining unit 38a, based on the chromaticity signal, acquires color information of the image data, such as a color shade or average color of the image data, and determines whether the capsule endoscope 2 has reached the predetermined portion of the subject 1 or not, based on this color information.

As explained above, according to the first embodiment of the invention, at least one of the plurality of receiving antennas for receiving the radio signal from the capsule endoscope is defined as a specified receiving antenna and arranged at a specified position of the subject (the position where the radio signal from the capsule endoscope before reaching the predetermined portion outside the subject can be received with high sensitivity, such as on the body surface in the neighborhood of the esophagus). The remaining antennas are dispersively arranged outside the subject (the position on the body surface corresponding to the passage of the capsule endoscope from the stomach to the large intestine, for example) other than the specified position. Also, during the period before the capsule endoscope introduced into the subject reaches the predetermined portion (such as the stomach) of the subject, the operation is switched to and maintained at the specified receiving antenna among the plurality of receiving antennas, so that the radio signal from the capsule endoscope before reaching the predetermined portion is constantly received through the specified receiving antenna. During the period after the capsule endoscope reaches the predetermined portion of the subject before being discharged out of the body, the radio signal from the capsule endoscope that has reached the predetermined portion is received from the receiving antenna most suitable for receiving the radio signal switched to among the plurality of receiving antennas. As a result, the radio signal from the capsule endoscope before reaching the predetermined portion of the subject can be received with high sensitivity through the specified receiving antenna, and the radio signal from the capsule endoscope after reaching the predetermined portion can be received with high sensitivity through any one of the plurality of receiving antennas. During the period after the capsule endoscope is swallowed into the subject before it is discharged out of the body, therefore, the radio signal can be received from the capsule endoscope with satisfactory sensitivity through the receiving antenna highest in received field strength among the plurality of receiving antennas. Consequently, the image data in satisfactory state can be certainly acquired in the subject including the image data on the interior of the esophagus imaged by the capsule endoscope while passing through it within as short a period as 4 seconds.

Modification of First Embodiment

Next, the receiving apparatus and the in-vivo information acquiring system using the apparatus according to a modification of the first embodiment of the invention will be explained. In the receiving apparatus and the in-vivo information acquiring system using the apparatus according to the modification of the first embodiment, a monitor device for monitoring and displaying the image data acquired by the receiving apparatus for receiving the radio signal from the capsule endoscope 2 is connected to the receiving apparatus, and information on the image data detected by the monitor device is fed back to the receiving apparatus. The receiving apparatus, based on the information on the image data fed back by the monitor device, determines whether the capsule endoscope 2 has reached the predetermined portion of the subject 1 or not.

Figure 6:
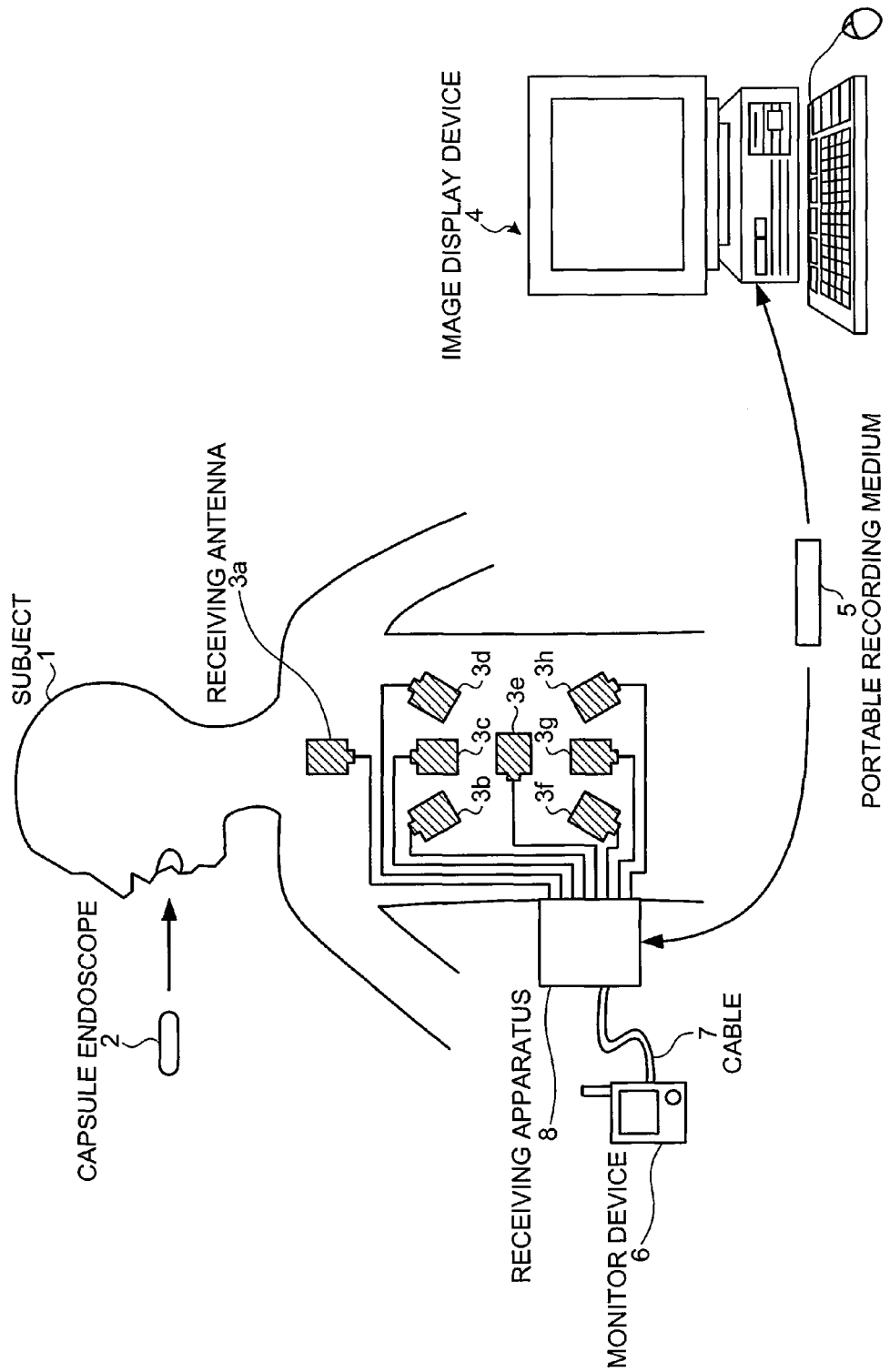
FIG. 6 is a schematic diagram schematically showing an example of the configuration of an in-vivo information acquiring system according to a modification of the first embodiment of the invention.

FIG. 6 is a schematic diagram schematically showing an example of the configuration of the in-vivo information acquiring system according to the modification of the first embodiment of the invention. As shown in FIG. 6, the in-vivo information acquiring system according to the modification of the first embodiment of the invention includes a receiving apparatus 8 in place of the receiving apparatus 3 of the in-vivo information acquiring system according to the first embodiment, and further, a monitor device 6 for sequentially monitoring and displaying image data picked up by the capsule endoscope 2 and acquired by the receiving apparatus 8. The monitor device 6 and the receiving apparatus 8 are connected to each other in a way adapted to transmit and receive the image data, etc. therebetween through a cable 7. The other parts of the configuration are identical with those of the first embodiment, and the same component parts are designated by the same reference numerals, respectively.

Figure 7:
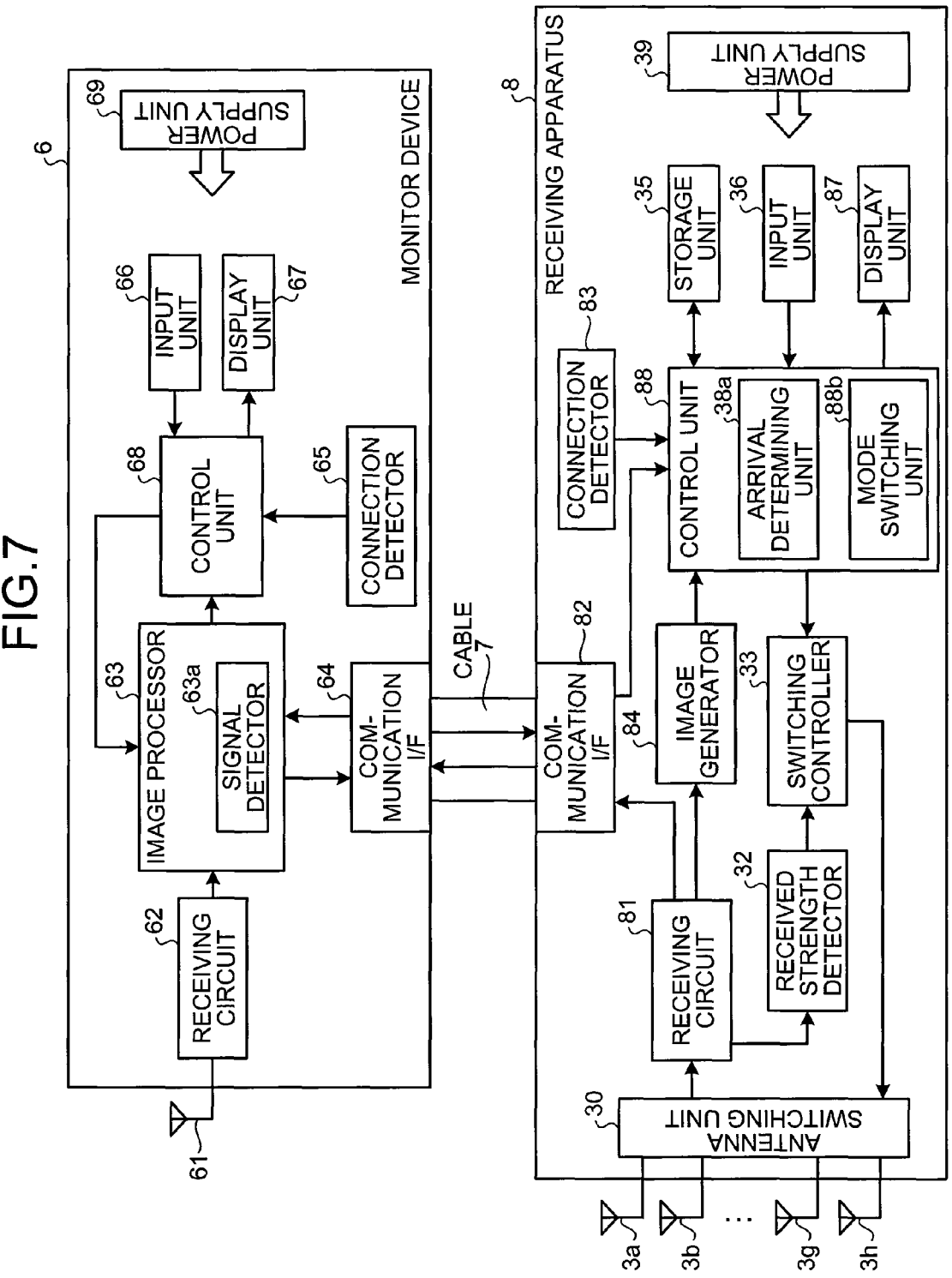
FIG. 7 is a block diagram schematically showing an example of the configuration of a receiving apparatus and a monitor device configuring a part of the in-vivo information acquiring system according to the modification of the first embodiment of the invention.

FIG. 7 is a block diagram schematically showing an example of the configuration of the receiving apparatus and the monitor device configuring a part of the in-vivo information acquiring system according to the modification of the first embodiment of the invention. As shown in FIG. 7, the monitor device 6 includes a receiving antenna 61 for receiving a radio signal from the capsule endoscope 2, a receiving circuit 62 for demodulating the radio signal received through the receiving antenna 61 into an image signal, and an image processor 63 for generating image data due to the capsule endoscope 2 based on the image signal demodulated by the receiving circuit 62. Also, the monitor device 6 includes a communication interface (I/F) 64 for connecting the receiving apparatus 8 and the monitor device 6 in a communicable way through the cable 7, and a connection detector 65 for detecting the connection between the receiving apparatus 8 and the monitor device 6 through the cable 7. The monitor device 6 further includes an input unit 66 for inputting the instruction information for instructing a control unit 68, a display unit 67 for monitoring and displaying the image data, etc., the control unit 68 for controlling the drive of each component part of the monitor device 6, and a power supply unit 69 for supplying the driving power to each component part of the monitor device 6.

In the case where the receiving apparatus 8 and the monitor device 6 are not connected to each other, the receiving antenna 61 and the receiving circuit 62 receive a radio signal from the capsule endoscope 2, and acquire the image data due to the capsule endoscope 2 based on the radio signal. Specifically, the receiving antenna 61 receives a radio signal from the capsule endoscope 2 and outputs the received radio signal to the receiving circuit 62. The receiving circuit 62 demodulates the radio signal received through the receiving antenna 61 into an image signal, and outputs the image signal thus obtained to the image processor 63.

The image processor 63 performs a predetermined image processing or the like on the image signal demodulated by the receiving circuit 62 or the image signal received through the receiving apparatus 8, and generates image data based on the image signal. The image data thus generated by the image processor 63 is the image data included in the radio signal received from the capsule endoscope 2 by the monitor device 6 alone through the receiving antenna 61 or the image data based on the image signal received through the receiving apparatus 8. The image processor 63 outputs the image data thus obtained to the control unit 68.

Also, the image processor 63 includes a signal detector 63*a* functioning in a way similar to the signal detector 34*a* of the receiving apparatus 3 described above. Based on the image signal received from the receiving apparatus 8 through the cable 7, the signal detector 63*a* detects information on the image data such as the brightness information of the image data. In this case, the signal detector 63*a*, based on the image signal, detects a brightness signal corresponding to the brightness information of the image data and feeds back the detected bright information to the receiving apparatus 8.

The communication I/F 64 is for connecting the receiving apparatus 8 and the monitor device 6 in a communicable way through the cable 7. Specifically, the communication I/F 64 is connected to the receiving apparatus 8 through the cable 7 so as to receive an image signal from the receiving apparatus 8 through the cable 7 output the received image signal to the image processor 63. Also, the communication I/F 64 outputs the brightness signal detected by the signal detector 63*a* to the receiving apparatus 8 through the cable 7. As a result, the brightness signal (i.e. the information on the image data) detected by the signal detector 63*a* is fed back to the receiving apparatus 8 that has acquired the image data.

The connection detector 65 is for detecting the connection between the receiving apparatus 8 and the monitor device 6. Specifically, the connection detector 65 detects the establishment of connection between the receiving apparatus 8 and the monitor device 6 by detecting the electrical conduction due to the connection between the receiving apparatus 8 and the monitor device 6 through the cable 7. Upon detection of the connection between the receiving apparatus 8 and the monitor device 6, the connection detector 65 outputs the detection result notifying the connection to the control unit 68.

The input unit 66 is implemented by using an input button, etc. for inputting the instruction information for instructing the control unit 68, and inputs the instruction information, etc. for giving an instruction to drive each component part to the control unit 68 in accordance with the input operation of the user. The display unit 67 is implemented by using a thin display such as a liquid crystal display device or an organic EL panel, and monitors and displays the information as instructed by the control unit 68 to display, for example, the image data based on the image signal received from the receiving apparatus 8 through the cable 7 or the image data, etc. acquired without the intermediary of the receiving apparatus 8. Incidentally, the display unit 67 may have an information input function such as the touch panel and may input the instruction information for instructing the control unit 68 to the control unit 68.

The control unit 68 is implemented by use of a CPU for executing a processing program, a ROM having stored therein the processing program, etc. in advance and a RAM for storing operation parameters or input information to the control unit 68, and controls the drive of each component part of the monitor device 6. In this case, the control unit 68 controls the information input/output with each component part while at the same time controlling the monitor display operation of the display unit 67 and the detecting operation of the connection detector 65.

Also, upon receipt of the detection result from the connection detector 65 to the effect that the connection between the receiving apparatus 8 and the monitor device 6 is detected, the control unit 68 controls the communication I/F 64 to transfer the image signal transmitted from the receiving apparatus 8 through the cable 7 to the image processor 63, and based on the image signal from the receiving apparatus 8, controls the image processor 63 to generate the image data. Further, the control unit 68 detects a brightness signal based on the image signal from the receiving apparatus 8, and controls the signal detector 63*a* and the communication I/F 64 to feed back the brightness signal to the receiving apparatus 8.

The power supply unit 69 has a power supply switch (not shown) for switching the on/off state of the driving power supply. In the case where the power supply switch is turned on, the power supply unit 69 supplies the driving power to each component part of the monitor device 6. Incidentally, a dry battery, a lithium secondary battery or a nickel hydrogen battery can be used, for example, as the power supply of the power supply unit 69. Also, the power supply unit 69 may be of charged type.

On the other hand, the receiving apparatus 8 according to a modification of the first embodiment of the invention, as shown in FIG. 7, includes a receiving circuit 81 in place of the receiving circuit 31, an image generator 84 in place of the image processor 34, a display unit 87 in place of the display unit 37 and a control unit 88 in place of the control unit 38 of the receiving apparatus 3 according to the first embodiment described above. The receiving apparatus 8 further includes a communication I/F 82 for making a connecting to the monitor device 6 through the cable 7 and a connection detector 83 for detecting the connection between the monitor device 6 and the receiving apparatus 8 through the cable 7. The other parts of the configuration are similar to those of the first embodiment, and the same component parts are designated by the same reference numerals, respectively.

The receiving circuit 81, like the receiving circuit 31 described above, demodulates a radio signal input from the capsule endoscope 2 through the antenna switching unit 30 into an image signal constituting a baseband signal, and outputs the image signal thus obtained to the received strength detector 32, the communication I/F 82 and the image generator 84.

The communication I/F 82 is connected to the communication I/F 64 of the monitor device 6 through the cable 7 to transmit and receive the data between the monitor device 6 and the receiving unit 8 through the cable 7. Specifically, the communication I/F 82 transmits the image signal demodulated by the receiving circuit 81 to the communication I/F 64 of the monitor device 6 through the cable 7, and receives, through the cable 7, information (such as a brightness signal) on the image data detected by the signal detector 63*a* of the monitor device 6. The communication I/F 82 outputs the information from the monitor device 6, such as the brightness signal, to the control unit 88.

The connection detector 83 is for detecting the connection between the receiving apparatus 8 and the monitor device 6. Specifically, the connection detector 83 detects that the receiving apparatus 8 and the monitor device 6 are connected to each other, by detecting the electrical conduction caused by the connection between the receiving apparatus 8 and the monitor device 6 through the cable 7. The connection detector 83, upon detection of the connection between the receiving apparatus 8 and the monitor device 6, outputs the detection result indicating the detection of the connection to the control unit 88.

The image generator 84, substantially similar to the image processor 34 described above, is for generating image data included in a radio signal received from the capsule endoscope 2 through any one of the plurality of receiving antennas 3*a* to 3*h*. Specifically, the image generator 84 executes a predetermined image processing on the image signal demodulated by the receiving circuit 81, and generates image data due to the capsule endoscope 2 based on the image signal. The image generator 84 outputs the image data thus obtained to the control unit 88.

The display unit 87 is implemented by use of a thin display such as a liquid crystal display device or an organic EL panel, and displays the information instructed by the control unit 88 to display, for example, information (patient name, patient ID, etc.) on the subject 1. Incidentally, the display unit 87 has an information input function such as a touch panel, and may be configured to input the instruction information to the control unit 88 in place of the input unit 36. In this case, the receiving apparatus 8 may have not the input unit 36.

The control unit 88 has the configuration and the function substantially similar to those of the control unit 38, and controls the drive of each component part of the receiving apparatus 8. Also, in the case where the power supply unit 39 begins to supply the driving power and the receiving apparatus 8 and the monitor device 6 are connected to each other, the control unit 88 sets the control mode of the switching controller 33 to the initial mode described above. Upon determination that the capsule endoscope 2 has reached the predetermined portion of the subject 1, on the other hand, the control unit 88 switches the control mode of the switching controller 33 from the initial mode to the normal mode described above.

The control unit 88 has the arrival determining unit 38*a* described above and a mode switching unit 88*b* in place of the mode switching unit 38*b* of the control unit 38 described above. In the case where step S101 detects that the driving power has begun to be supplied by the power supply unit 39 and the detection information indicating the detection of connection between the receiving apparatus 8 and the monitor device 6 is received from the connection detector 83, then the control unit 88 sets the control mode of the switching controller 33 to the initial mode. In this case, the mode switching unit 88*b*, like in the first embodiment, sets the control mode of the switching controller 33 to the initial mode by using, as a trigger, the fact that the power supply unit 39 has begun to supply the driving power and the detection information indicating the detection of connection between the receiving apparatus 8 and the monitor device 6.

Incidentally, in the case where the control unit 88 has not acquired the detection information indicating the detection of connection between the receiving apparatus 8 and the monitor device 6, the mode switching unit 88*b* sets the control mode of the switching controller 33 to the normal mode. Specifically, in the case where the receiving apparatus 8 and the monitor device 6 are not connected to each other, the switching controller 33 controls the normal antenna switching operation of the antenna switching unit 30 in the normal mode described above.

On the other hand, the control unit 88 determines in step S102 whether the capsule endoscope 2 has reached the predetermined portion of the subject 1 or not, based on the brightness signal fed back from the monitor device 6. In this case, the arrival determining unit 38*a* acquires the brightness signal fed back from the signal detector 63*a* of the monitor device 6, and like in the first embodiment described above, determines whether the capsule endoscope 2 has reached the predetermined portion of the subject 1 or not. In the case where the arrival determining unit 38*a* determines that the capsule endoscope 2 has reached the predetermined portion (such as the stomach) of the subject 1, the control unit 88 switches the control mode of the switching controller 33 from the initial mode to the normal mode. In this case, the mode switching unit 88*b*, like in step S103 described above, switches the control mode of the switching controller 33 to the normal mode by using, as a trigger, the determination by the arrival determining unit 38*a* that the capsule endoscope 2 has reached the stomach that is the predetermined portion of the subject 1.

Incidentally, according to the modification of the first embodiment of the invention, the brightness information of the image data is detected as the information on the image data to determine whether the capsule endoscope 2 has reached the predetermine portion of the subject 1 or not. Nevertheless, the invention is not limited to this configuration, but color information of the image data may be detected in place of the brightness information. In this case, the signal detector 63*a* detects a chromaticity signal corresponding to color information of the image data based on the image signal, and feeds back the detected chromaticity signal to the control unit 88. The arrival determining unit 38*a*, based on this chromaticity signal, acquires color information of the image data, such as a color shade or an average color of the image data, and determines whether the capsule endoscope 2 has reached the predetermined portion of the subject 1 or not, based on the color information.

As explained above, the modification of the first embodiment of the invention has a substantially similar function to the first embodiment. Further, the monitor device for sequentially monitoring and displaying the image data acquired by the receiving apparatus is connected to the receiving apparatus, and a detection function for detecting the information on the image data such as the brightness information or the color information is added to the monitor device. The information on the image data detected by the monitor device is fed back to the receiving apparatus, and based on the information on the image data fed back to the receiving apparatus, it is determined whether the capsule endoscope has reached the predetermined portion of the subject or not. As a result, a receiving apparatus and an in-vivo information acquiring system using the receiving apparatus are easily realized in which the operational effects of the first embodiment described above can be enjoyed on the one hand, and the image data in the satisfactory state can be certainly acquired in the subject including the image data on the interior of the esophagus picked up by the capsule endoscope while passing therethrough within a time as short as about 4 seconds on the other hand.

Second Embodiment

Next, a second embodiment of the invention will be explained. In the first embodiment described above, it is determined whether the capsule endoscope has reached a predetermined portion of the subject or not, based on the information on the image data such as the brightness information or the color information detected based on the image signal. According to the second embodiment, on the other hand, an imaging interval of image data is switched before and after a capsule endoscope reaches a predetermined portion of a subject. The imaging interval of the image data is detected based on an image signal from the capsule endoscope, and it is determined whether the capsule endoscope has reached the predetermined portion of the subject or not, based on the detected change in the imaging interval.

Figure 8:
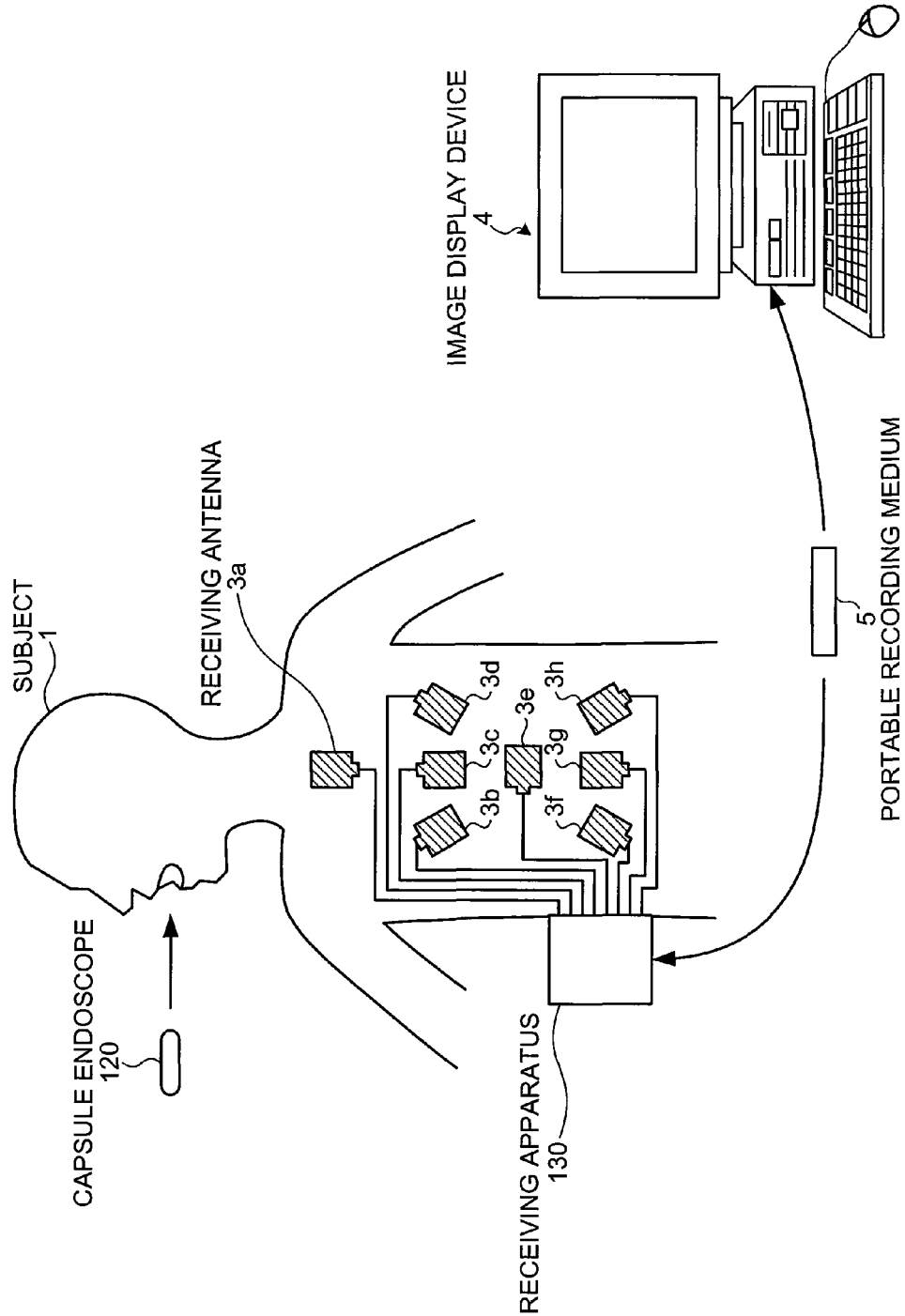
FIG. 8 is a schematic diagram schematically showing an example of the configuration of an in-vivo information acquiring system according to a second embodiment of the invention.

FIG. 8 is a schematic diagram schematically showing an example of the configuration of an in-vivo information acquiring system according to the second embodiment of the invention. As shown in FIG. 8, the in-vivo information acquiring system according to the second embodiment of the invention includes a capsule endoscope 120 in place of the capsule endoscope 2 of the in-vivo information acquiring system according to the first embodiment and a receiving apparatus 130 in place of the receiving apparatus 3. The other component parts are identical with those of the first embodiment, and the same component parts are designated by the same reference numerals, respectively.

Figure 9:
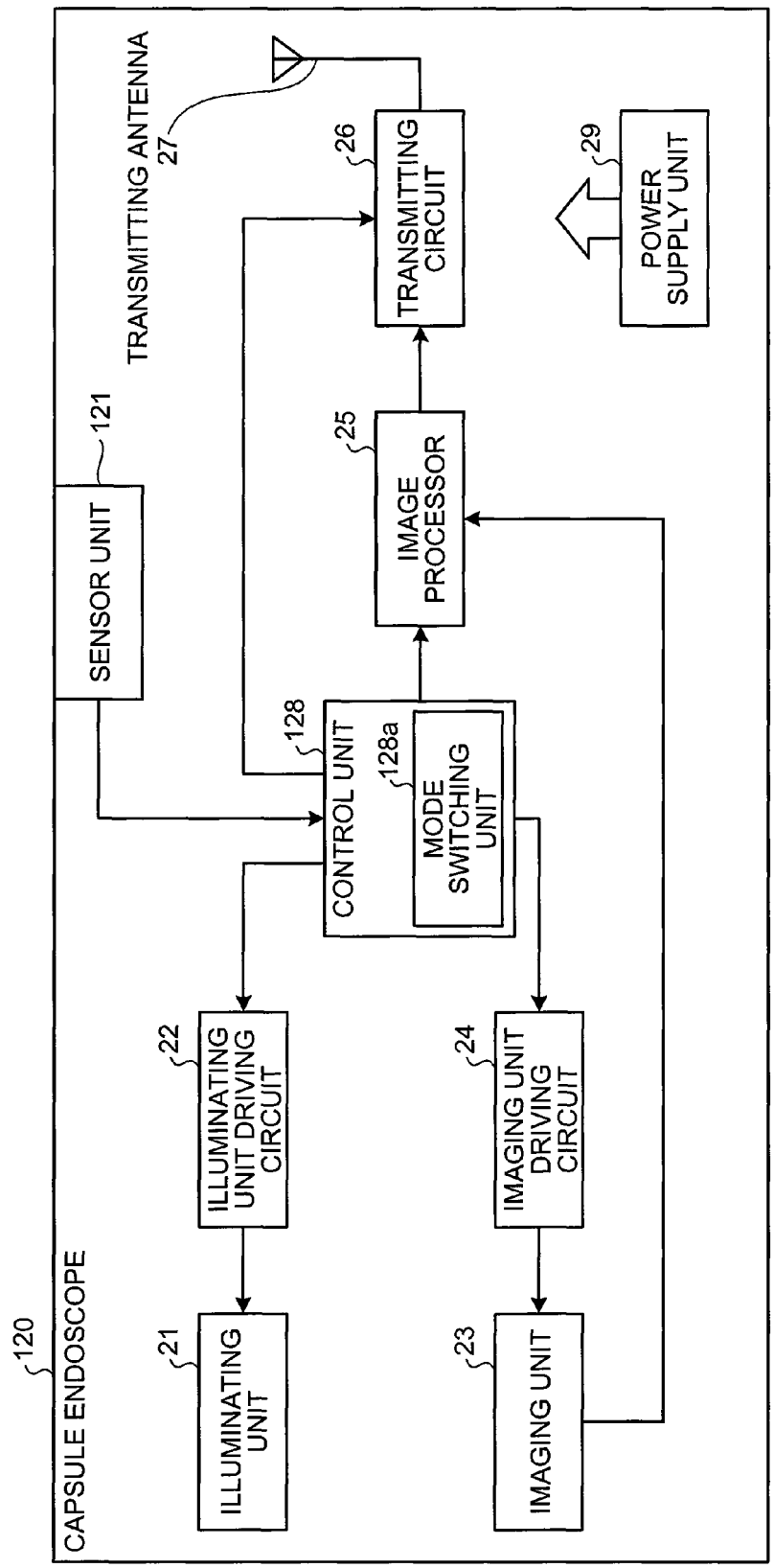
FIG. 9 is a block diagram schematically showing an example of the configuration of a capsule endoscope configuring a part of the in-vivo information acquiring system according to the second embodiment of the invention.

FIG. 9 is a block diagram schematically showing an example of the configuration of the capsule endoscope configuring a part of the in-vivo information acquiring system according to the second embodiment of the invention. As shown in FIG. 9, the capsule endoscope 120 includes a control unit 128 in place of the control unit 28 of the capsule endoscope 2 of the in-vivo information acquiring system according to the first embodiment described above, and further has a sensor unit 121 for detecting a current position of the capsule endoscope 120 in the subject 1. The other component parts are identical with those of the first embodiment, and the same component parts are designated by the same reference numerals, respectively.

The sensor unit 121 is for detecting a current position of the capsule endoscope 120 introduced into the subject 1. Specifically, the sensor unit 121 is implemented by using, for example, a pH sensor, and measures a pH value at the current position of the capsule endoscope 120 introduced into the subject 1 and detects the current position of the capsule endoscope 120 based on the pH value thus obtained. In this case, the sensor unit 121 detects whether the current position of the capsule endoscope 120 represents a predetermined portion (such as the stomach) of the subject 1 or not. The sensor unit 121 outputs to the control unit 128 the result of detecting whether the current position of the capsule endoscope 120 represents the predetermined portion of the subject 1 or not.

The control unit 128 has a function substantially similar to that of the control unit 28 of the capsule endoscope 2 described above, and controls the drive of each component part of the capsule endoscope 120. Also, the control unit 128 performs the control operation to switch an imaging mode of the imaging unit 23 on the one hand and the control operation to switch the drive of the illuminating unit 21 in accordance with the imaging mode of the imaging unit 23 on the other hand. The control unit 128 has a mode switching unit 128a for controlling the imaging unit driving circuit 24 to switch the imaging mode of the imaging unit 23 to a fast imaging mode or a normal imaging mode.

The mode switching unit 128a controls the imaging unit driving circuit 24 by using, as a trigger, the fact that the power supply unit 29 has begun to supply the driving power and sets the imaging mode of the imaging unit 23 to the fast imaging mode providing the initial state. In this case, the control unit 128 controls the illuminating unit driving circuit 22 and the imaging unit driving circuit 24 in such a manner that the imaging timing of the imaging unit 23 and the illumination timing of the illuminating unit 21 are synchronized with each other in the fast imaging mode. Thereafter, in the case where the control unit 128 receives the detection result from the sensor unit 121 to the effect that the current position of the capsule endoscope 120 represents the predetermined portion of the subject 1, the mode switching unit 128a controls the imaging unit driving circuit 24 with the detection result as a trigger, and switches the imaging mode of the imaging unit 23 from the fast imaging mode to the normal imaging mode. In this case, the control unit 128 controls the illuminating unit driving circuit 22 and the imaging unit driving circuit 24 in such a manner that the imaging timing of the imaging unit 23 and the illumination timing of the illuminating unit 21 are synchronized with each other in the normal imaging mode.

Incidentally, in the normal imaging mode, the imaging unit 23 picks up the image data at predetermined intervals of, for example, about 0.5 seconds, while the fast imaging mode is such that the imaging unit 23 picks up the image data at shorter intervals of, for example, about 0.07 seconds than in the normal imaging mode. This fast imaging mode is suitable for imaging the portion such as the esophagus through which the capsule endoscope 120 passes within a short length of time, while the normal imaging mode is suitable for imaging the portion such as the stomach, the small intestine or the large intestine where it takes a comparatively long time for the capsule endoscope 120 to pass through.

The capsule endoscope 120 employing this configuration, during the period from the time when it is swallowed from the mouth of the subject 1 to the time when it reaches the predetermined portion, i.e. the stomach, images the interior (such as the esophagus) of the subject 1 in the fast imaging mode described above, and with the arrival at the stomach and thereafter, switches to the normal imaging mode described above from the fast imaging mode until the capsule endoscope 120 is discharged out of the subject 1 thereby to image the interior (such as the stomach, the small intestine or the large intestine) of the subject 1 in the normal imaging mode. The capsule endoscope 120 can pick up many image data of the portion such as the esophagus passed in a short time of about 4 seconds, while at the same time picking up an appropriate number, but not an excessively great number, of frames of the image data of the portion such as the small intestine or the large intestine where it takes a long time to pass through, thereby promoting the power saving effect.

Figure 10:
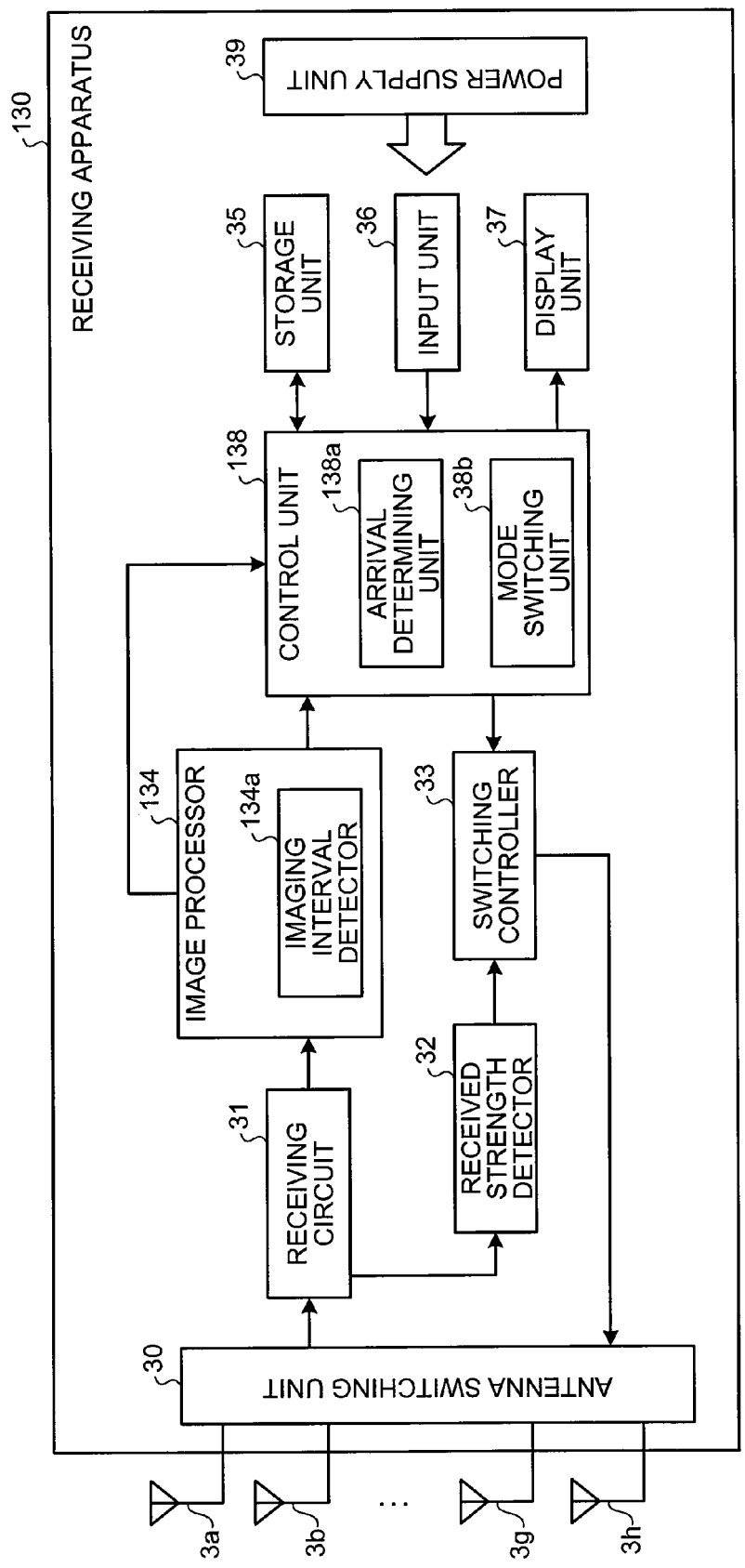
FIG. 10 is a block diagram schematically showing an example of the configuration of the receiving apparatus according the second embodiment of the invention.

FIG. 10 is a block diagram schematically showing an example of the configuration of the receiving apparatus configuring a part of the in-vivo information acquiring system according to the second embodiment of the invention. As shown in FIG. 10, the receiving apparatus 130 includes an image processor 134 in place of the image processor 34 of the receiving apparatus 3 and a control unit 138 in place of the control unit 38 according to the first embodiment. The other component parts of the configuration are identical with those of the first embodiment, and the same component parts are designated by the same reference numerals, respectively.

The image processor 134, like the image processor 34 of the receiving apparatus 3 described above, executes a predetermined image processing or the like on the image signal demodulated by the receiving circuit 31, and generates image data based on the image signal. The image processor 134 outputs the image data thus obtained to the control unit 138. Also, the image processor 134 includes an imaging interval detector 134a. The imaging interval detector 134a, based on the image signal demodulated by the receiving circuit 31, detects the imaging interval of the image data due to the capsule endoscope 120. In this case, the imaging interval detector 134a detects in which imaging mode, the fast imaging mode or the normal imaging mode, the image data based on the image signal is picked up. This imaging interval detector 134a outputs the image data imaging interval detection result to the control unit 138.

The control unit 138, having a substantially similar function to the control unit 38 of the receiving apparatus 3 described above, controls the drive of each component part of the receiving apparatus 130. Also, in the case where the power supply unit 39 has begun to supply the driving power, the control unit 138 sets the control mode of the switching controller 33 to the initial mode described above, and thereafter, switches the control mode of the switching controller 33 from the initial mode to the normal mode in the case where the image data generated by the image processor 134 changes from the one picked up in the fast imaging mode to the one picked up in the normal imaging mode.

The control unit 138 includes the mode switching unit 38b, and an arrival determining unit 138a in place of the arrival determining unit 38a of the control unit 38 described above. Based on the imaging interval detection result from the imaging interval detector 134a, the arrival determining unit 138a determines whether the capsule endoscope 120 has reached the predetermined portion, i.e. the stomach of the subject 1 or not.

Specifically, the control unit 138 executes the process of step S101 so as to set the control mode of the switching controller 33 to the initial mode. Next, the control unit 138 determines, in step S102, whether the capsule endoscope 120 has reached the predetermined portion (such as the stomach) of the subject 1 or not, based on the imaging interval detection result from the imaging interval detector 134a.

In this case, the arrival determining unit 138a, based on the imaging interval detection result from the imaging interval detector 134a, sequentially grasps in which imaging mode, the fast imaging mode or the normal imaging mode, the image data input from the image processor 134 is picked up, and determines that the capsule endoscope 120 has reached the stomach, i.e. the predetermined portion of the subject 1 by using, as a trigger, the change of the image data of the image processor 134 from the fast imaging mode to the normal imaging mode.

Upon determination by the arrival determining unit 138a that the capsule endoscope 120 has reached the predetermined portion, i.e. the stomach of the subject 1, the control unit 138 executes the process of step S103 described above so as to switch the control mode of the switching controller 33 from the initial mode to the normal mode. In this case, the mode switching unit 38b switches the control mode of the switching controller 33 to the normal mode by using, as a trigger, the determination by the arrival determining unit 138a that the capsule endoscope 120 has reached the predetermine portion, i.e. the stomach of the subject 1. Specifically, the mode switching unit 38b switches the control mode of the switching controller 33 in accordance with the switch of the imaging mode of the capsule endoscope 120.

As described above, according to the second embodiment of the invention, substantially similar to the first embodiment described above, the radio signal is received from the capsule endoscope by switching to a specified one of the plurality of receiving antennas. In addition, the imaging interval of the image data is detected in place of the information on the image data, and it is determined, based on the imaging interval detection result, whether the capsule endoscope has reached the predetermined portion (such as the stomach) of the subject or not. Upon determination that the capsule endoscope has reached the predetermined portion, substantially similarly to the first embodiment described above, the radio signal is received from the capsule endoscope by switching to the specified one or the remaining ones of the plurality of receiving antennas. As a result, a receiving apparatus and an in-vivo information acquiring system using the receiving apparatus can be realized which can enjoy the operational effects of the first embodiment and can certainly acquire the image data in a satisfactory state in the subject including many image data on the interior of the esophagus imaged by the capsule endoscope in the fast imaging mode while passing through the esophagus within as short a time as about 4 seconds.

Third Embodiment

Next, a third embodiment of the invention will be explained. According to the first embodiment described above, it is determined whether the capsule endoscope has reached the predetermined portion of the subject or not, based on the information on the image data such as the brightness information or the color information detected from the image signal. According to the third embodiment, on the other hand, a capsule endoscope measures a pH value at a current position in a subject, the pH value is detected based on an image signal from the capsule endoscope, and based on the pH value thus detected, it is determined whether the capsule endoscope has reached a predetermined portion of the subject or not.

Figure 11:
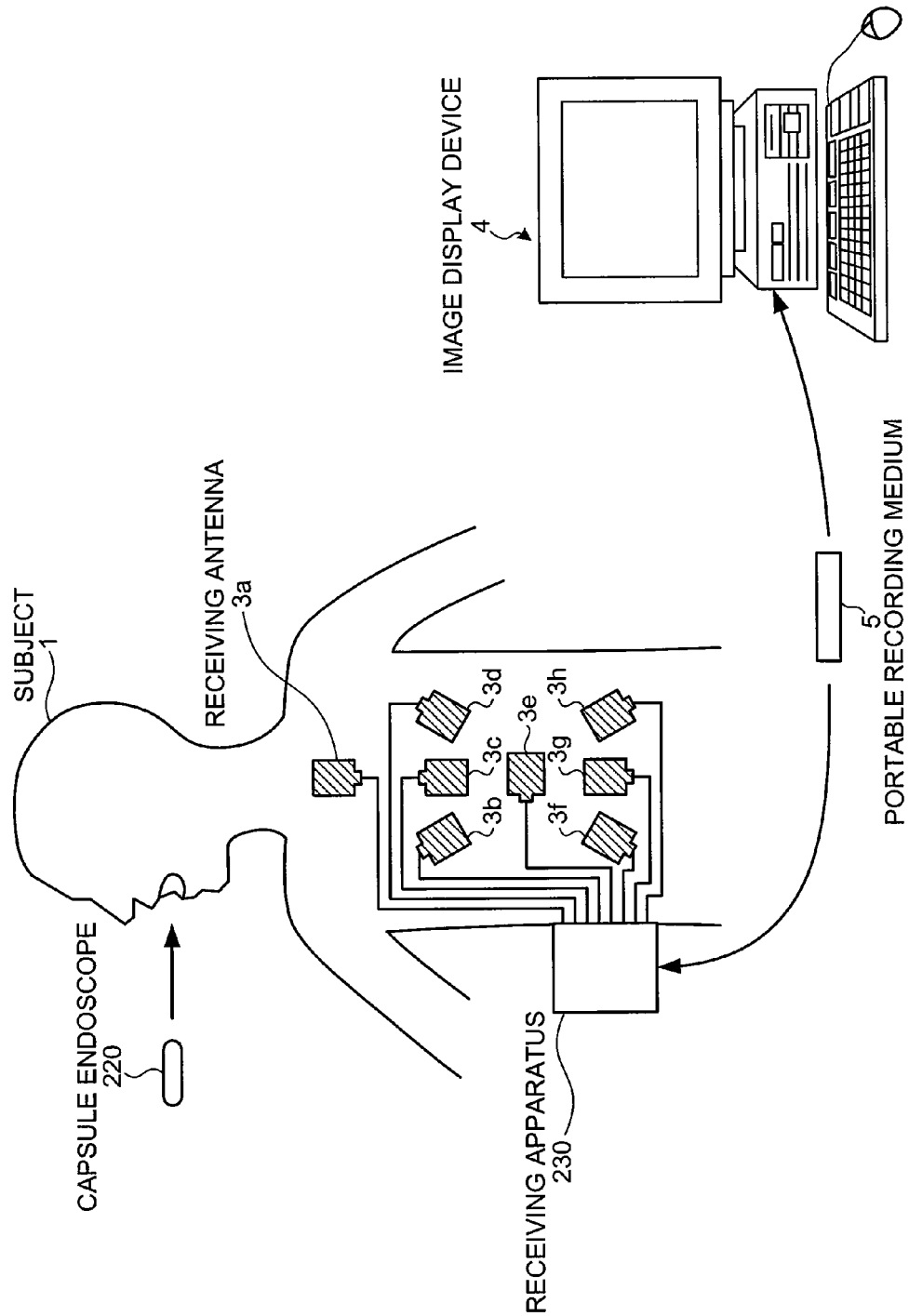
FIG. 11 is a schematic diagram schematically showing an example of the configuration of an in-vivo information acquiring system according to a third embodiment of the invention.

FIG. 11 is a schematic diagram schematically showing an example of the configuration of an in-vivo information acquiring system according to the third embodiment of the invention. As shown in FIG. 11, the in-vivo information acquiring system according to the third embodiment of the invention includes a capsule endoscope 220 in place of the capsule endoscope 2 of the in-vivo information acquiring system according to the first embodiment described above and a receiving apparatus 230 in place of the receiving apparatus 3. The other component parts are identical with those of the first embodiment, and the same component parts are designated by the same reference numerals, respectively.

Figure 12:
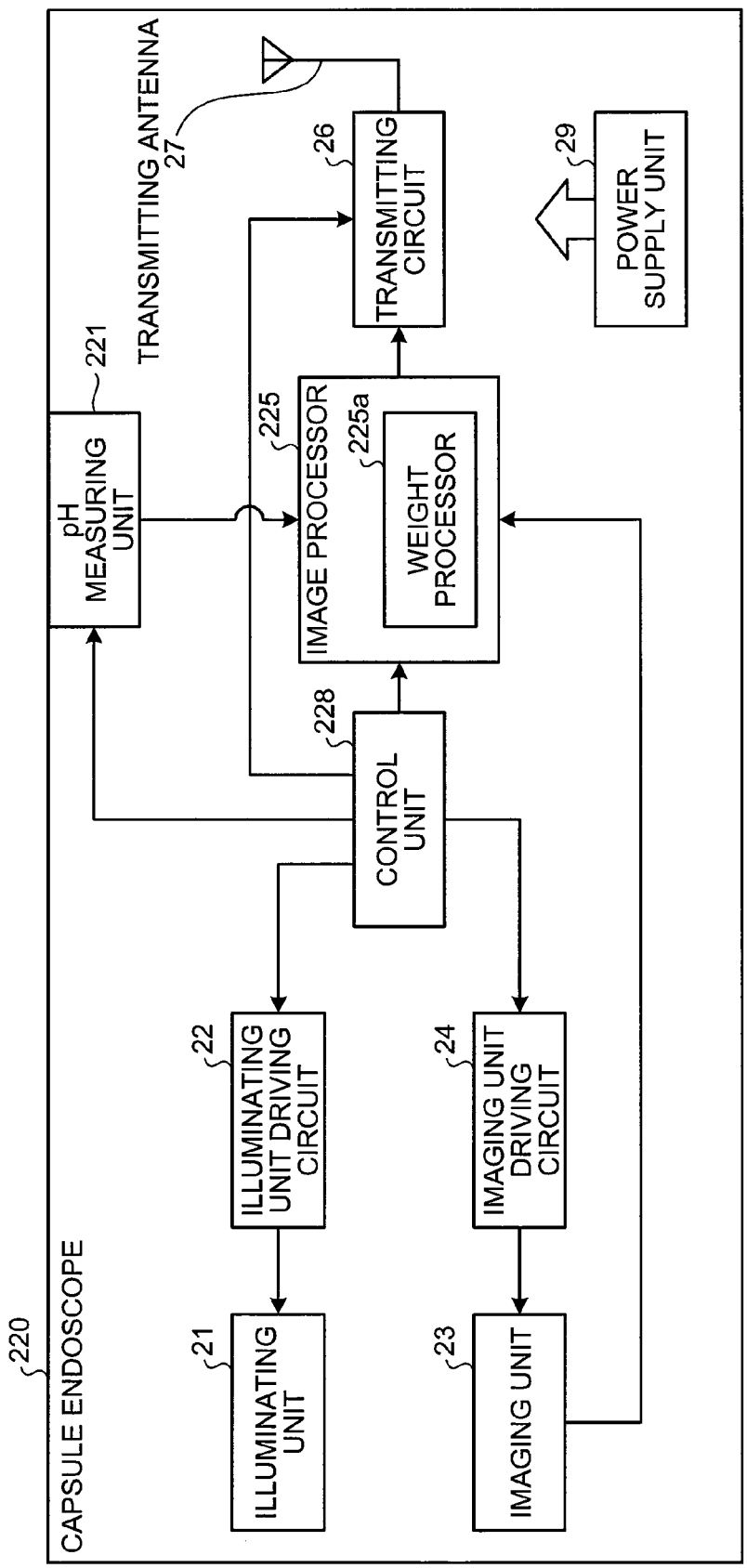
FIG. 12 is a block diagram schematically showing an example of the configuration of a capsule endoscope configuring a part of the in-vivo information acquiring system according to the third embodiment of the invention.

FIG. 12 is a block diagram schematically showing an example of the configuration of a capsule endoscope configuring a part of the in-vivo information acquiring system according to the third embodiment of the invention. As shown in FIG. 12, the capsule endoscope 220 includes an image processor 225 in place of the image processor 25 of the capsule endoscope 2 and a control unit 228 in place of the control unit 28 of the in-vivo information acquiring system according to the first embodiment described above. Also, the capsule endoscope 220 includes a pH measuring unit 221 for measuring a pH value at a current position of the capsule endoscope 220 in the subject 1. The other component parts of the configuration are identical with those of the first embodiment, and the same component parts are designated by the same reference numerals, respectively.

The pH measuring unit 221 is implemented by use of, for example, a hydrogen ion-sensitive field effect transistor, and sequentially measures at predetermined intervals the pH value at the current position of the capsule endoscope 220 introduced into the subject 1. In this case, the pH measuring unit 221 can measure the pH value at the current position of the capsule endoscope 220 by detecting a current generated due to the absorption of hydrogen ions (i.e. hydrogen ions existing at the current position of the capsule endoscope 220) to a gate electrode of the hydrogen ion-sensitive field effect transistor. The pH measuring unit 221 sequentially outputs the measurement result signal corresponding to the pH value obtained to the image processor 225.

The image processor 225, substantially similar to the image processor 25 arranged in the capsule endoscope 2 according to the first embodiment described above, functions to generate an image signal including image data picked up by the imaging unit 23. Also, the image processor 225 includes a superimposing processor 225a for superimposing (adding) the pH value measured by the pH measuring unit 221 on the image signal. The superimposing processor 225a superimposes the measurement result signal from the pH measuring unit 221 on the image signal including the image data picked up by the imaging unit 23, whereby the pH value measured by the pH measuring unit 221 is further superimposed on the image signal. In this case, the image processor 225 generates an image signal including at least the image data picked up by the imaging unit 23 and the pH value measured by the pH measuring unit 221 and outputs the image signal thus obtained to the transmitting circuit 26.

The control unit 228 has a substantially similar function to the control unit 28 of the capsule endoscope 2 described above, and controls the drive of each component part of the capsule endoscope 220. The control unit 228 controls the pH measuring operation of the pH measuring unit 221 in accordance with the imaging timing of the imaging unit 23, for example, while at the same time controlling the drive to generate the image signal including at least the image data picked up by the imaging unit 23 and the pH value measured by the pH measuring unit 221.

By the control operation of the control unit 228, the image signal including the image data and the pH value is modulated into a radio signal by the transmitting circuit 26 and output to an external part through the transmitting antenna 27. In this way, the capsule endoscope 220 can transmit the image data and the pH value as a radio signal to the external receiving apparatus 230.

Figure 13:
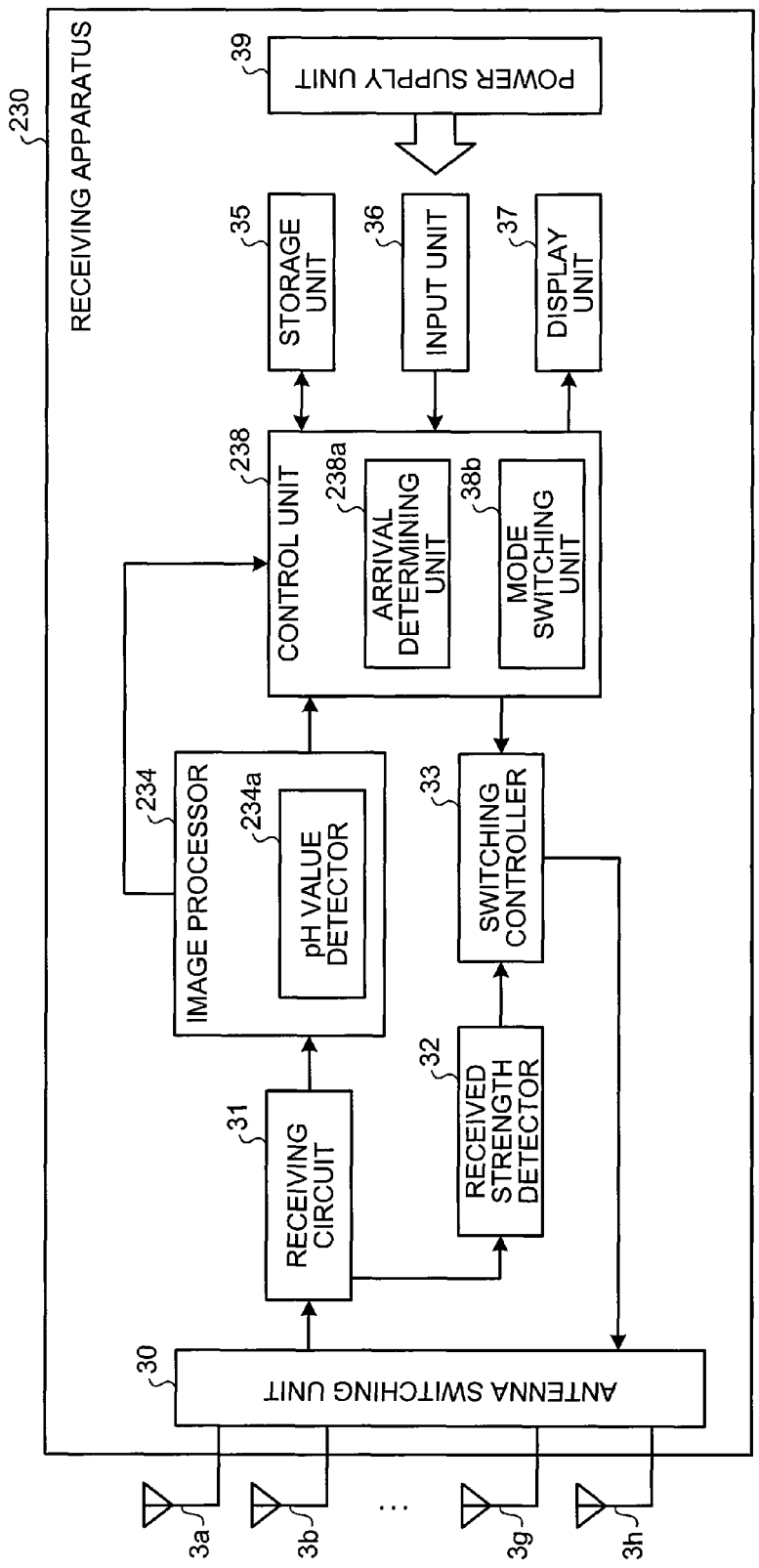
FIG. 13 is a block diagram schematically showing an example of the configuration of a receiving apparatus according the third embodiment of the invention.

FIG. 13 is a block diagram schematically showing an example of the configuration of a receiving apparatus configuring a part of the in-vivo information acquiring system according to the third embodiment of the invention. As shown in FIG. 13, the receiving apparatus 230 includes an image processor 234 in place of the image processor 34 of the receiving apparatus 3 and a control unit 238 in place of the control unit 38 according to the first embodiment described above. The other component parts are identical with those of the first embodiment, and the same component parts are designated by the same reference numerals, respectively.

The image processor 234, like the image processor 34 of the receiving apparatus 3 described above, executes a predetermined image processing on an image signal demodulated by the receiving circuit 31, and generates image data based on the image signal. The image processor 234 outputs the image data thus obtained to the control unit 238. Also, the image processor 234 includes a pH value detector 234a for detecting a pH value included in the image signal.

The pH value detector 234a is for detecting the pH value based on the image signal demodulated by the receiving circuit, i.e. the pH value measured by the pH value measuring unit 221 of the capsule endoscope 220 described above. Specifically, the pH value detector 234a detects a measurement result signal superimposed on the image signal demodulated by the receiving circuit 31, and then detects a pH value corresponding to the measurement result signal. The pH value detector 234a outputs the pH value thus detected (i.e. the pH value at the current position of the capsule endoscope 220) to the control unit 238.

The control unit 238 has a function substantially similar to that of the control unit 38 of the receiving apparatus 3 described above, and controls the drive of each component part of the receiving apparatus 230. Also, in the case where the power supply unit 39 has begun to supply the driving power, the control unit 238 sets the control mode of the switching controller 33 to the initial mode described above. Thereafter, in the case where the pH value detected by the pH value detector 234a is not higher than a predetermined threshold value, i.e. in the case where the acidity at the current position of the capsule endoscope 220 is not less than a predetermined level, the control unit 238 switches the control mode of the switching controller 33 from the initial mode to the normal mode.

The control unit 238 includes the mode switching unit 38b described above and also an arrival determining unit 238a in place of the arrival determining unit 38a of the control unit 38 described above. The arrival determining unit 238a determines whether the capsule endoscope 220 has reached a predetermined portion of the subject 1, based on the pH value detected by the pH value detector 234a, i.e. the pH value at the current position of the capsule endoscope 220.

Specifically, the control unit 238 executes the process of step S101 described above so as to set the control mode of the switching controller 33 to the initial mode. Next, the control unit 238 determines, in step S102 described above, whether the capsule endoscope 220 has reached the predetermined portion (such as the stomach) of the subject 1 or not, based on the pH value detected by the pH value detector 234a.

In this case, the arrival determining unit 238a compares the pH value detected by the pH value detector 234a with a preset predetermined threshold value. In the case where the pH value is not higher than a predetermined threshold value, i.e. in the case where the acidity at the current position of the capsule endoscope 220 is not less than a predetermined level, the arrival determining unit 238a determines that the capsule endoscope 220 has reached the predetermined portion, i.e. the stomach of the subject 1.

In the case where the arrival determining unit 238a determines that the capsule endoscope 220 has reached the predetermined portion, i.e. the stomach of the subject 1, the control unit 238 executes the process of step S103 described above so as to switch the control mode of the switching controller 33 from the initial mode to the normal mode. In this case, the mode switching unit 38b switches the control mode of the switching controller 33 to the normal mode by using, as a trigger, the determination by the arrival determining unit 238a that the capsule endoscope 220 has reached the predetermined portion, i.e. the stomach of the subject 1. In other words, the mode switching unit 38b switches the control mode of the switching controller 33 in response to the fact that the acidity at the current position of the capsule endoscope 220 has reached a predetermined level.

As explained above, according to the third embodiment of the invention, substantially similarly to the first embodiment described above, a radio signal from the capsule endoscope is received by switching to a specified one of a plurality of receiving antennas. Also, the pH value at the current position of the capsule endoscope is detected in place of the information on the image data described above, and based on this pH value, it is determined whether the capsule endoscope has reached a predetermined portion (such as the stomach) of the subject. Upon determination that the capsule endoscope has reached the predetermined portion of the subject, substantially similarly to the first embodiment described above, the radio signal is received from the capsule endoscope by switching to the specified one or the remaining ones of the plurality of receiving antennas. As a result, a receiving apparatus and an in-vivo information acquiring system using the receiving apparatus can be realized in which the operational effects of the first embodiment described above can be enjoyed and which can certainly determine whether the capsule endoscope introduced into the subject has reached the predetermined portion, i.e. the stomach.

Fourth Embodiment

Next, a fourth embodiment of the invention will be explained. In the first embodiment described above, it is determined whether the capsule endoscope has reached a predetermined portion of the subject or not, based on the information on the image data such as the brightness information or the color information detected based on the image signal. According to the fourth embodiment, on the other hand, a time elapsed after switching to a specified one of a plurality of receiving antennas is measured, and based on the elapsed time, it is determined whether the capsule endoscope has reached a predetermined portion of the subject or not.

Figure 14:
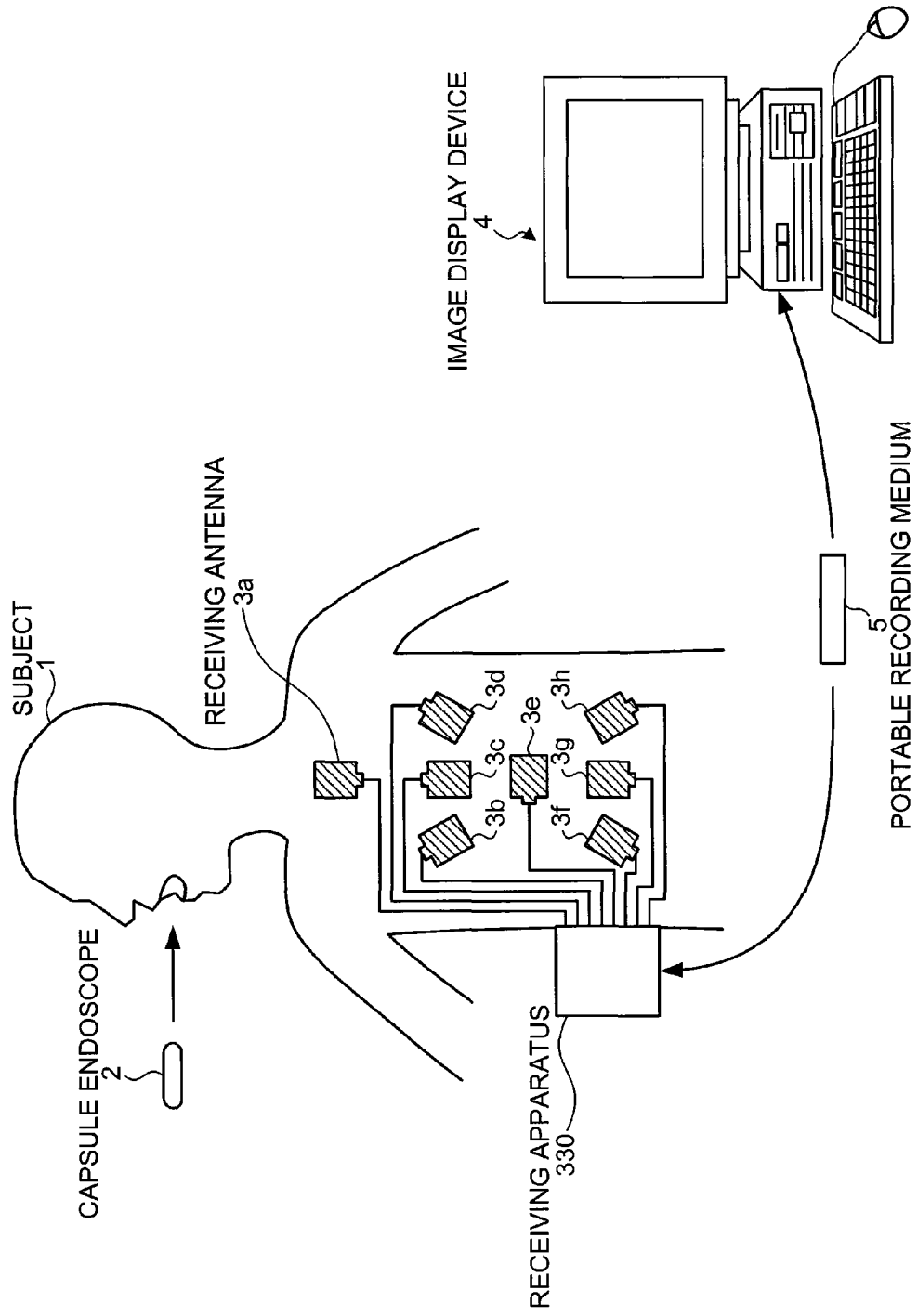
FIG. 14 is a schematic diagram schematically showing an example of the configuration of an in-vivo information acquiring system according to a fourth embodiment of the invention.

FIG. 14 is a schematic diagram schematically showing an example of the configuration of an in-vivo information acquiring system according to the fourth embodiment of the invention. As shown in FIG. 14, the in-vivo information acquiring system according to the fourth embodiment of the invention includes a receiving apparatus 330 in place of the receiving apparatus 3 of the in-vivo information acquiring system according to the first embodiment described above. The other component parts are identical with those of the first embodiment, and the same component parts are designated by the same reference numerals, respectively.

Figure 15:
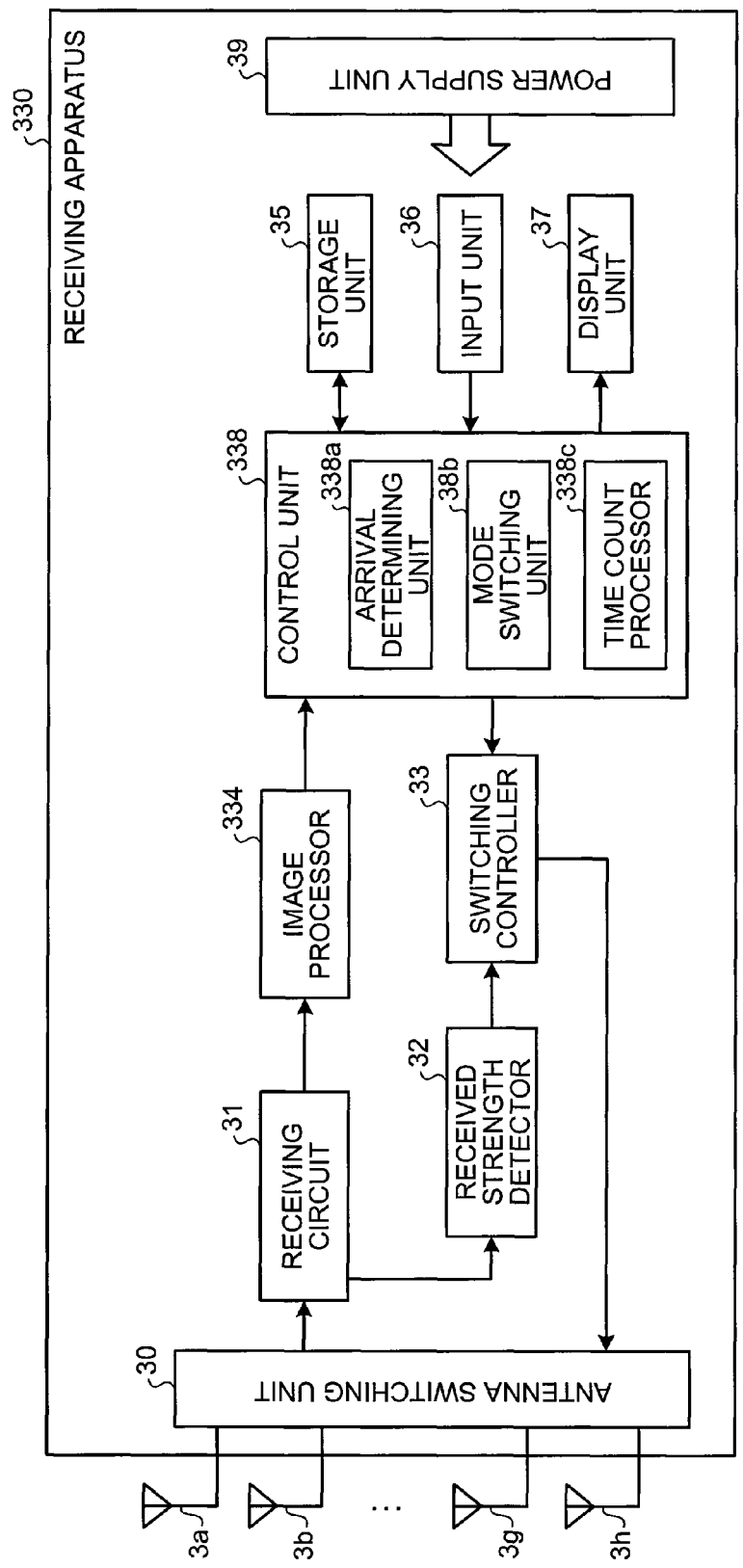
FIG. 15 is a block diagram schematically showing an example of the configuration of a receiving apparatus according the fourth embodiment of the invention.

FIG. 15 is a block diagram schematically showing an example of the configuration of a receiving apparatus configuring a part of the in-vivo information acquiring system according to the fourth embodiment of the invention. As shown in FIG. 15, the receiving apparatus 330 includes an image processor 334 in place of the image processor 34 of the receiving apparatus 3 and a control unit 338 in place of the control unit 38 according to the first embodiment described above. The other component parts are identical with those of the first embodiment, and the same component parts are designated by the same reference numerals, respectively.

The image processor 334, like the image processor 34 of the receiving apparatus 3 described above, executes a predetermined image processing on an image signal demodulated by the receiving circuit 31, and generates image data based on the image signal. The image processor 334 outputs the image data thus obtained to the control unit 338.

The control unit 338 has a function substantially similar to that of the control unit 38 of the receiving apparatus 3 described above, and controls the drive of each component part of the receiving apparatus 330. Also, in the case where the power supply unit 39 has begun to supply the driving power, the control unit 338 sets the control mode of the switching controller 33 to the initial mode described above, while at the same time functioning to measure a time elapsed from the switching of the antenna switching unit 30 to a specified receiving antenna (i.e. the receiving antenna 3a) by the control operation in the initial mode. Further, in the case where the time elapsed after the switching to the receiving antenna 3a (i.e. the time elapsed after switching to the specified receiving antenna) has reached a predetermined threshold value, the control unit 338 switches the control mode of the switching controller 33 from the initial mode to the normal mode.

The control unit 338 includes the mode switching unit 38b described above and also an arrival determining unit 338a in place of the arrival determining unit 38a of the control unit 38 described above. Further, the control unit 338 includes a time count processor 338c for measuring the time elapsed after switching to the receiving antenna 3a among the plurality of receiving antennas 3a to 3h by the antenna switching unit 30.

The arrival determining unit 338a determines whether the capsule endoscope 220 has reached the predetermined portion of the subject 1 or not, based on the elapsed time measured by the time count processor 338c, i.e. the time elapsed after switching to the receiving antenna 3a constituting the specified receiving antenna among the plurality of receiving antennas 3a to 3h.

The time count processor 338c functions to measure the time elapsed after the antenna switching unit 30 switches to the receiving antenna 3a under the control of the switching controller 33. In this case, the time count processor 338c starts counting the time by using, as a trigger, the fact that the driving power has begun to be supplied by the power supply unit 39, for example, and measures the time elapsed after the driving power begins to be supplied, i.e. the time elapsed after the antenna switching unit 30 switches to the receiving antenna 3a under the control of the switching controller 33 set to the initial mode described above. The time count processor 338c notifies the arrival determining unit 338a of the elapsed time thus measured.

Specifically, the control unit 338 executes the process of step S101 described above so as to set the control mode of the switching controller 33 to the initial mode. In this case, the time count processor 338c starts the time counting process by using, as a trigger, the fact that the power supply unit 39 has begun to supply the driving power, and measures the time elapsed after the antenna switching unit 30 switches to the receiving antenna 3a among the plurality of receiving antennas 3a to 3h under the control of the switching controller 33 in the initial mode.

Next, the control unit 338 determines, in step S102 described above, whether the capsule endoscope 2 has reached the predetermined portion (such as the stomach) of the subject 1 or not, based on the elapsed time notified from the time count processor 338c. In this case, the arrival determining unit 338a determines whether the elapsed time measured by the time count processor 338c has reached a predetermined threshold time, and upon determination that the elapsed time has reached the predetermined threshold time, determines that the capsule endoscope 2 has reached the predetermined portion, i.e. the stomach of the subject 1.

The elapsed time measured by the time count processor 338c is the time elapsed after the power supply unit 39 begins to supply the driving power as described above, i.e. the time elapsed after the antenna switching unit 30 switches to the receiving antenna 3a among the plurality of receiving antennas 3a to 3h under the control of the switching controller 33 in the initial mode. Incidentally, the capsule endoscope 2 is generally swallowed from the mouth of the subject 1 immediately before or after the power supply switch of the power supply unit 39 is turned on. In this case, the elapsed time measured by the time count processor 338c corresponds to the time during which the capsule endoscope 338c introduced into the subject 1 moves. The arrival determining unit 338a, therefore, determines that the capsule endoscope 2 has reached the stomach through the esophagus of the subject 1, based on the fact that the elapsed time measured by the time count processor 338c (i.e. the time during which the capsule endoscope 2 moves) has reached a predetermined threshold time.

Upon determination by the arrival determining unit 338a that the capsule endoscope 2 has reached the predetermined portion, i.e. the stomach of the subject 1, the control unit 338 executes the process of step S103 described above so as to switch the control mode of the switching controller 33 from the initial mode to the normal mode. In this case, the mode switching unit 38b switches the control mode of the switching controller 33 to the normal mode by using, as a trigger, the determination by the arrival determining unit 338a that the capsule endoscope 2 has reached the predetermined portion, i.e. the stomach of the subject 1. Specifically, the mode switching unit 38b switches the control mode of the switching controller 33 in response to the fact that time during which the capsule endoscope 2 introduced into the subject 1 moves reaches the predetermined threshold time.

As explained above, according to the fourth embodiment of the invention, substantially similar to the first embodiment described above, the radio signal is received from the capsule endoscope by switching to a specified one of a plurality of receiving antennas. Also, in place of the information on the image data described above, the time elapsed after switching to the specified receiving antenna is measured, and based on the measured elapsed time (i.e. the time during which the capsule endoscope introduced into the subject moves), it is determined whether the capsule endoscope has reached a predetermined portion (such as the stomach) of the subject or not. Upon determination that the capsule endoscope has reached the predetermined portion, substantially similarly to the first embodiment, the radio signal is received from the capsule endoscope by switching to the specified receiving antenna or the remaining receiving antennas among the plurality of receiving antennas. As a result, a receiving apparatus that can enjoy the operational effects of the first embodiment described above and an in-vivo information acquiring system using the receiving apparatus are easily realized.

According to the first to fourth embodiments and the modification of the first embodiment, the one receiving antenna 3a among the plurality of receiving antennas 3a to 3h is defined as a specified receiving antenna arranged at a specified position of the subject 1. The invention, however, is not limited to such a configuration, but two or more ones of the plurality of receiving antennas can be defined as specified receiving antennas.

Also, according to the first to fourth embodiments and the modification of the first embodiment, the radio signal from the capsule endoscope is received through a specified one of a plurality of receiving antennas before a predetermined portion (such as the stomach) of the subject is reached, and after reaching the predetermined portion of the subject, the radio signal from the capsule endoscope is received by the remaining receiving antennas. The invention, however, is not limited to such a configuration, but the radio signal may be received from the capsule endoscope, after reaching the predetermined portion of the subject, through a receiving antenna (a receiving antenna suitable for the radio signal) to which the radio signal is switched among all the receiving antennas including the specified receiving antenna.

INDUSTRIAL APPLICABILITY

As described above, the receiving apparatus and the in-vivo information acquiring system using the receiving apparatus according to the invention are useful for acquiring various data (in-vivo information) such as an image of the organs in a subject. Especially, the invention is applicable to the receiving apparatus and the in-vivo information acquiring system using the receiving apparatus capable of certainly acquiring, with high sensitivity, in-vivo information transmitted by radio from the capsule endoscope introduced into the subject even in the case where it passes through the organs within a short time.

The invention claimed is:

1. A receiving apparatus comprising:
   a plurality of receiving antennas that receive a radio signal from a mobile unit movable in a subject, data on the interior of the subject being acquired based on the radio signal received through any one of the plurality of receiving antennas, the plurality of receiving antennas including a specified receiving antenna that is specified in advance from the plurality of receiving antennas as an antenna for receiving the radio signal from the mobile unit until the mobile unit reaches a predetermined portion in the subject;
   a switching controller that performs an antenna switching control operation in two modes which are an initial mode and a normal mode, wherein the switching controller, in the initial mode, switches the receiving antenna that receives the radio signal to the specified receiving antenna and maintains a state in which only the specified antenna receives the radio signal, and the switching controller, in the normal mode selects any one of the plurality of receiving antennas in accordance with a predetermined condition every time the radio signal is received and switches the receiving antenna that receives the radio signal to the selected one of the plurality of receiving antennas;
   a determining unit that determines whether the mobile unit has reached the predetermined portion in the subject or not; and
   a mode switching unit that instructs the switching controller to perform the antenna switching control operation in the initial mode until the determining unit determines that the mobile unit has reached the predetermined portion in the subject, the mode switching unit instructing the switching controller to perform the antenna switching control operation by switching the initial mode to the normal mode, when the determining unit determines that the mobile unit has reached the predetermined portion in the subject.

2. The receiving apparatus according to claim 1, comprising a detector that detects information on the data included in the radio signal,
   wherein the determining unit determines whether the mobile unit has reached the predetermined portion in the subject or not, based on the information on the data detected by the detector.

3. The receiving apparatus according to claim 2, wherein the data is image data imaged by the mobile unit.

4. The receiving apparatus according to claim 3, wherein the information on the data is one of brightness information, chromaticity information, and an imaging interval of the image data.

5. The receiving apparatus according to claim 1, wherein the predetermined portion is the stomach of the subject.

6. The receiving apparatus according to claim 1, comprising a received strength detector that detects a received electric-field strength of the radio signal,
    wherein the switching controller performs the antenna switching control operation in the normal mode for switching to the receiving antenna having the highest received electric-field strength of the radio signal among at least the plurality of receiving antennas.

* * * * *

UNITED STATES PATENT AND TRADEMARK OFFICE
CERTIFICATE OF CORRECTION

PATENT NO.      : 8,632,457 B2  
APPLICATION NO. : 12/090688  
DATED           : January 21, 2014  
INVENTOR(S)     : Nagase et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1676 days.

Signed and Sealed this
Twenty-second Day of September, 2015

Michelle K. Lee
*Director of the United States Patent and Trademark Office*